United States Patent [19]

Glaug et al.

[11] Patent Number: 5,711,832

[45] Date of Patent: Jan. 27, 1998

[54] PROCESS FOR MAKING A TRAINING PANT HAVING A SEPARATE WAIST ELASTIC SYSTEM

[75] Inventors: Frank Steven Glaug; Margaret Ann Kato, both of Appleton, Wis.

[73] Assignee: Kimberly-Clark Worldwide, Inc., Neenah, Wis.

[21] Appl. No.: 456,239

[22] Filed: May 31, 1995

[51] Int. Cl.⁶ .................... A41B 9/14; A61F 13/15; B32B 31/04; B32B 31/08

[52] U.S. Cl. .................... 156/73.1; 2/401; 2/402; 156/164; 156/204; 156/269; 156/290; 156/297; 156/308.4; 604/385.2; 604/396

[58] Field of Search .................... 156/163–164, 156/73.1, 182, 204, 222, 226–227, 269, 290–291, 297, 299–303, 308.4, 229, 160, 161; 604/285.1, 385.2, 393, 396; 2/400, 401, 402

[56] References Cited

U.S. PATENT DOCUMENTS

| | | |
|---|---|---|
| Re. 23,040 | 9/1948 | Rand . |
| D. 315,630 | 3/1991 | Larsen . |
| D. 338,543 | 8/1993 | van Lear . |
| D. 339,633 | 9/1993 | Porter . |
| 462,965 | 11/1891 | Darby . |
| 1,397,579 | 11/1921 | Guinzburg . |
| 2,016,355 | 10/1935 | Alsop . |
| 2,678,648 | 5/1954 | de Woskin . |
| 2,976,199 | 3/1961 | Rand .................... 156/163 |
| 3,048,176 | 8/1962 | de Woskin . |
| 3,150,665 | 9/1964 | May, Jr. et al. . |
| 3,225,764 | 12/1965 | Magid . |
| 3,237,625 | 3/1966 | Johnson . |
| 3,368,563 | 2/1968 | Scheier . |
| 3,560,292 | 2/1971 | Butter .................... 2/402 X |
| 3,608,551 | 9/1971 | Seijo . |
| 3,613,687 | 10/1971 | Kennedy . |
| 3,663,962 | 5/1972 | Burger .................... 2/402 |
| 3,828,367 | 8/1974 | Bourgeois .................... 156/164 X |
| 4,031,568 | 6/1977 | Huff .................... 2/402 X |
| 4,227,952 | 10/1980 | Sabee . |
| 4,581,772 | 4/1986 | Smith . |
| 4,639,949 | 2/1987 | Ales et al. . |
| 4,641,381 | 2/1987 | Heran et al. . |
| 4,642,818 | 2/1987 | Dehnert et al. . |
| 4,726,873 | 2/1988 | Ales et al. . |
| 4,735,622 | 4/1988 | Acuff et al. . |
| 4,786,346 | 11/1988 | Ales et al. . |
| 4,820,164 | 4/1989 | Kemper . |
| 4,940,464 | 7/1990 | Van Gompel et al. . |
| 4,946,539 | 8/1990 | Ales et al. . |
| 4,995,333 | 2/1991 | Keller et al. .................... 156/291 X |
| 5,064,421 | 11/1991 | Tracy . |
| 5,064,489 | 11/1991 | Ujimoto et al. . |
| 5,074,854 | 12/1991 | Davis . |
| 5,114,420 | 5/1992 | Igaue et al. . |
| 5,224,941 | 7/1993 | Simmons . |
| 5,292,316 | 3/1994 | Suzuki . |
| 5,340,648 | 8/1994 | Rollins et al. .................... 156/291 X |
| 5,545,275 | 8/1996 | Herrin et al. .................... 2/400 X |
| 5,601,547 | 2/1997 | Kato et al. .................... 604/385.2 |

FOREIGN PATENT DOCUMENTS

| | | | |
|---|---|---|---|
| 752160 | 12/1970 | Belgium .................... 156/227 |
| 0 320 991 A2 | 6/1989 | European Pat. Off. . |
| 6037481 A1 | 6/1994 | European Pat. Off. . |
| 1189649 | 10/1959 | France .................... 604/396 |
| 2082803 | 12/1971 | France .................... 2/402 |
| 3-205053 | 9/1991 | Japan .................... 604/396 |
| 6-54878 | 3/1994 | Japan .................... 604/396 |
| 6-197920 | 7/1994 | Japan .................... 604/396 |
| 2 283 662 A | 5/1995 | United Kingdom . |
| WO 94/28845 | 12/1994 | WIPO . |
| WO 95/00096 | 1/1995 | WIPO . |
| WO95/19258 | 7/1995 | WIPO . |

OTHER PUBLICATIONS

U.S. Patent Applicatiion Serial No. 08/306,353.
U.S. Patent Application Serial No. 08/267,272.
U.S. Patent Application Serial No. 08/264,539.

*Primary Examiner*—Adrienne C. Johnstone
*Attorney, Agent, or Firm*—Douglas L. Miller

[57] ABSTRACT

A process for making disposable absorbent articles including continuously moving a first layer in a first direction and a second layer in a second direction, continuously providing elongate elastic members to the first layer and to the second layer, folding the layers over the elongate elastic members, joining the elongate elastic members to the layers to form first and second continuous elastic composites, continuously moving a base layer having opposite edge portions, continuously delivering the first and the second continuous elastic composites to respective edge portions of the base layer, joining the first and the second continuous elastic composites to the edge portions of the base layer, providing a plurality of spaced apart absorbent structures on the base layer, folding the continuously moving base layer, bonding the folded base layer between the absorbent structures, and cutting the folded base layer to form a plurality of disposable absorbent articles.

8 Claims, 11 Drawing Sheets

PROCESS FOR MAKING A TRAINING PANT HAVING A SEPARATE WAIST ELASTIC SYSTEM

BACKGROUND OF THE INVENTION

The present invention pertains to a process for making disposable absorbent training pants for children, and more particularly to a process for making training pants having improved waist elastic systems therefor.

Current disposable absorbent training pants for children going through the potty training stage have proved to be a particularly desirable and useful product. This is especially true for the child, when he or she has outgrown, or believe they have outgrown, diapers. Diapers are for babies, and most children do not like being identified with or as babies. Consequently, these children do not want to wear baby diapers, and instead prefer to wear a training pant that looks like adult underwear.

One problem with current training pants, however, is that they do not provide optimum comfort and ease of use, i.e., ease of pulling up or pulling down, over a wide weight or size range and for an extended period of time. This discomfort, and difficulty in pulling up or pulling down, very often frustrates the child to the point that potty training is delayed due to the child's displeasure with and difficulty in using the product.

One reason current training pants do not provide optimum comfort and ease of use is the fact that one training pant size is intended for use by children within a particular range of weights or sizes. This requires a single size training pant to fit children with different size waists. In practice, this means that the training pant will not provide a substantially uniform low tension over the required waist size range. For example, one specific training pant size may be designed to fit children within a weight range of 25–35 pounds. This weight range includes a wide range of waist sizes. Generally, the training pant will fit one particular weight, i.e., intermediate waist size, well enough to provide some degree of satisfaction. However, at the low weight end, i.e., the smallest waist size, an elastic waistband must be used to gather the excess material at the waist opening. However, the tension provided by the retracted elastic waistband can be too high, thereby causing discomfort and/or difficulty in pulling the pant up or down for the smaller to intermediate size children.

At the high end of the weight range, where the waist size is largest, the elastic waistband will extend its maximum allowable length to accommodate the larger waist. However, when fully extended, it can exert too high of a tension against the child's waist. Again, this results in discomfort, possible redmarking, and difficulty in pulling the pant up and down, thereby delaying potty training.

Thus, the fact that a single size training pant is designed to fit wide weight ranges has prevented them from providing substantially uniform low tensions over the corresponding wide size ranges over an extended period of time. Yet, this is an extremely desirable feature which, if available, would provide a training pant comfortable to the child, and easy to pull up or down. Thus, as a child would grow into, and then out of, a specified weight range for a specific training pant size, then the child would have a substantially uniform force or tension at the waist during that period of wearing the specific size training pant; but, this feature is not available in current children's disposable absorbent training pants.

Various designs of elastic waistbands have been used in these training pants, such as a single wide elastic member or a plurality of narrow elastic members. The waistbands may fully, or only partially, surround the waist opening. Generally, these elastic waistbands are incorporated by one of two methods. The first method incorporates the elastic waistbands when they are in an extended, tensioned state. The second method incorporates the elastic waistbands while they are in a relaxed, untensioned state. The latter method may require the use of a special elastic material, such as a heat-elasticizable material.

In both of these methods, the elastic waistbands generally are joined to multiple layers of material. For example, the elastic waistbands can be adhesively joined between two adjacent layers of material, such as, for example, the topsheet and backsheet of the training pant. In some cases, the elastic waistbands are first adhesively joined to a carrier sheet of material, and then the carrier sheet and elastic waistbands are adhesively joined between the adjacent layers.

The application of adhesive in these methods is generally accomplished by partially or totally coating the mutually facing surfaces of the adjacent layers, or by applying the adhesive in a bead to at least one of the layers. The latter method usually involves a continuous bead pattern, such as a wave-like pattern of adhesive.

Other methods or patterns for applying adhesive are available, and include joining the elastic waistbands along their full or entire length to multiple layers of material.

SUMMARY OF THE INVENTION

In one form of the present invention there is provided a process of making disposable absorbent training pants comprising the steps of continuously moving a first layer, continuously providing an elastic member to the first layer, folding the first layer over the elastic member, continuously moving a second layer, continuously providing an elastic member to the second layer, folding the second layer over the elastic member, continuously moving a base layer, continuously delivering the folded first layer to an edge portion of the base layer, joining the first layer to the edge portion, continuously delivering the folded second layer to an opposite edge portion of the base layer, joining the second layer to the opposite edge portion, providing absorbent structures between the edge portions of the base layer, folding the moving base layer along a fold line, bonding the folded moving base layer along bond lines, and cutting the bonded moving base layer between the absorbent structures to form a plurality of disposable absorbent training pants.

DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings, wherein.

DEFINITIONS

Figure 1:
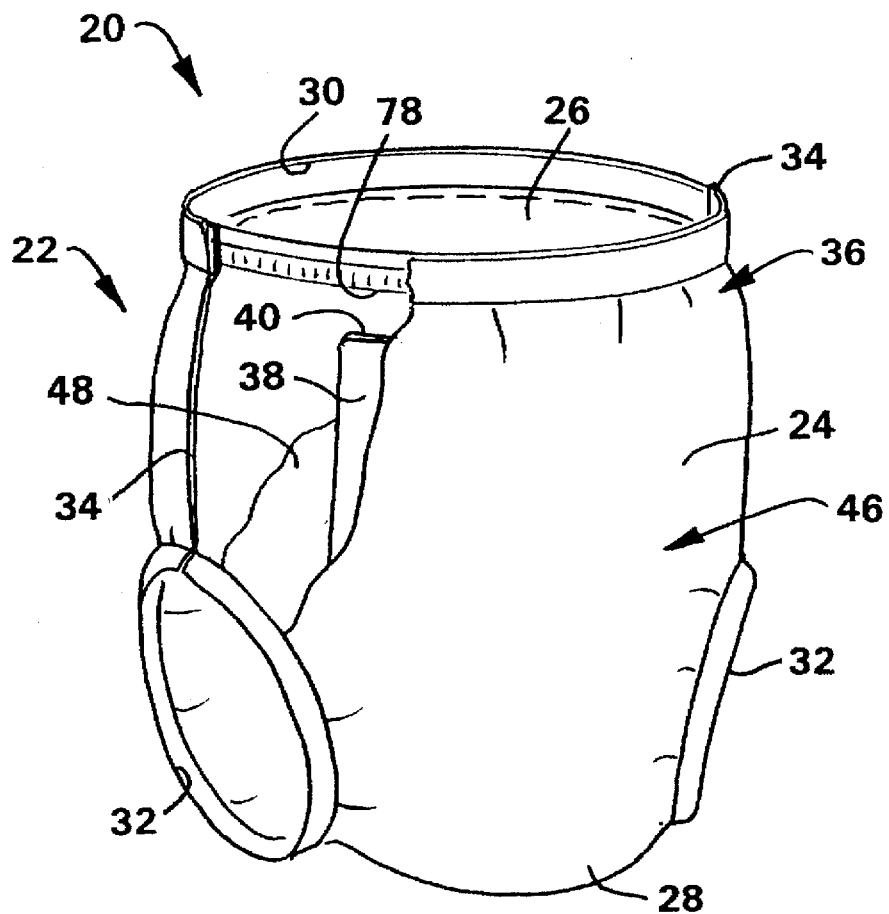
FIG. 1 is a partially broken-away, front perspective view of a child's training pant made in accordance with the principles of the present invention.

Within the context of this specification, each term or phrase below includes the following meaning or meanings. These terms may be further defined, or used in conjunction with additional language to further expand their meaning, in the specification.

(a) "Associated with" refers to the attachment of an elastic member, or elastic structure, to another element such that the elastic member, or elastic structure, when attached to, placed with, or formed from the element, gives that element elastic properties. Thus, the joined elastic member and the other element exhibit elasticity.

(b) "Cycle" refers to an extension of an elastic member or elastic structure, and a retraction of the elastic member or elastic structure following the removal of the force causing the extension.

(c) "Decay" refers to a loss of tension at a specific extension over a selected number of cycles.

(d) "Disposable" refers to a garment, article, pant, or the like, that is designed to be used until soiled, either by urination, defecation, or otherwise, and then discarded, rather than being washed and reused again.

(e) "Disposed", "disposed on", "disposed with", and variations thereof, refer to one element being integral or unitary with another element, or to one element being a separate structure joined to, connected to, placed with, or placed near another element.

(f) "Elasticity" refers to the tendency of a material, or composite material, to recover its original size and shape after removal of the force causing a deformation. Elasticity may be expressed in percent.

(g) "Elongation" refers to the ratio of the extension of a material to the length of a material prior to the extension, and is represented by the formula:

extended length minus original length/original length×100.

Elongation may be expressed as a percent.

(h) "Extension" or variations thereof refers to the change in length of a material due to stretching, and may be expressed in units of length.

(i) "Hysteresis" refers to a loss of tension over a specified number of cycles within a specified extension range.

(j) "Joining" or variations thereof refers to two or more elements being connected together in any suitable manner, such as by heat sealing, ultrasonic bonding, thermal bonding, adhesive bonding, stitching, or the like. The elements can be joined directly together, or may have one or more elements interposed between them, all of which are connected together.

(k) "Member" when used in the singular can have the dual meaning of a single element, or a plurality of elements.

(l) "Modulus of elasticity" refers to a constant that numerically measures or represents the amount of elasticity a material possesses.

(m) "Retraction" or variations thereof refers to the decreasing change in length of an extended material upon removal of the force causing the extension.

(n) "Elongate sleeve member" refers to a structure having an elongate passage therein. The sleeve member can be formed by one layer of material folded upon itself, or two or more layers of material being selectively joined together, to form the elongate passage.

(o) "Tension" refers to a force tending to cause the extension of a body, or to the balancing force within that body resisting the extension. Tension may be expressed in units of grams.

(p) "Waistborder" refers to a border about the waist opening of a training pant, and may be constructed of one or more layers of material.

DETAILED DESCRIPTION

The present invention provides a process for making an improved waist elastic system for children's training pants that results in a substantially uniform low tension along the peripheral border of the waist opening over a wide size range, a more comfortable fit, and improved ease of use by the child over an extended period of use. This is accomplished by, among other things, reducing the number of layers of material, i.e., the mass or amount of material, that the waist elastic system must gather. The more material there is to gather, the more the elasticity will be degraded or reduced in gathering the excess material. The present invention reduces this number of layers or amount of material to be gathered by incorporating an elastic member in, for example, one layer of material, thereby reducing loss of elasticity.

The present invention selectively reduces the joined surface area, or the number of points of joinder, between an elastic member and its respective layer to which it is joined. For example, the elastic member may not be attached along its full length to the layer. The present invention provides a plurality of selectively spaced apart, distinct adhesive zones. By reducing the surface area of joinder between the elastic member and the layer of material, there is a resultant reduction in the elastic member's loss of elasticity.

With reference to FIG. 1, a disposable absorbent training pant 20 comprises a chassis 22 including a front panel 24, a back panel 26, a crotch panel 28, a waist opening 30, and a pair of leg openings 32. Openings 30, 32 are formed by selectively joining portions of front panel 24 and back panel 26 at side seams 34, which extend between waist opening 30 and a respective leg opening 32. Each side seam 34 can be formed in any suitable manner, such as by ultrasonic bonding, thermal bonding, adhesive bonding, or the like. A waist border 36 peripherally surrounds waist opening 30, and is formed upon joining front panel 24 and back panel 26 at seams 34.

Figure 2:
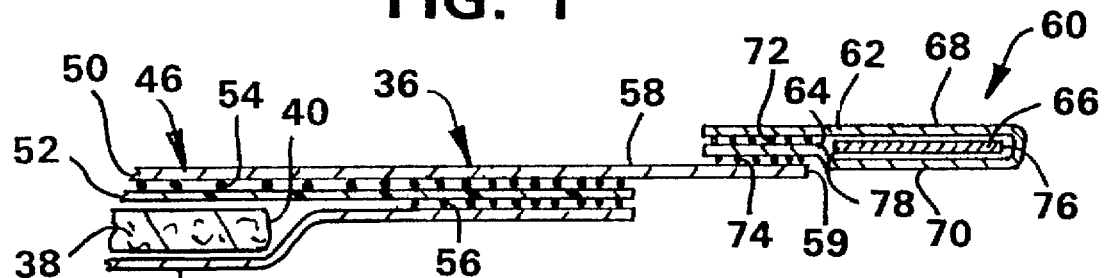
FIG. 2 is a cross-section through the waist of the pant in FIG. 1.

Referring now to FIGS. 1 and 2, chassis 22 includes an absorbent structure 38 disposed at least at crotch panel 28. Absorbent structure 38 includes an absorbent end edge 40, and has a length dimension 42 (FIG. 6) that is greater than a width dimension 44. Chassis 22 further includes an outer cover layer 46 and a liner 48, which sandwich absorbent structure 38 therebetween. Liner 48 is desirably a single layer of liquid permeable material, but may also include other layers of material. Outer cover layer 46 is desirably a two-layer material that includes an outer layer 50, which can be made of a nonwoven liquid permeable material, and an inner layer 52, which can be made of a liquid impermeable material. Outer layer 50 and inner layer 52 can be joined together in any suitable manner, such as by adhesives 54. Liner 48 is desirably joined to outer cover layer 46 by adhesives 56, thereby sandwiching absorbent structure 38 therebetween. As described, chassis 22 is a multi-layer structure comprising outer cover layer 46 and liner 48.

Waist border 36 (FIG. 2) may also be a multi-layer structure comprising outer cover layer 46 and liner 48. Waist border 36 desirably includes an extension of one of the layers of chassis 22, for example, an extension of outer layer 50 (FIG. 2). This extension forms a peripheral edge portion 58 that peripherally surrounds waist opening 30.

Although described above with reference to a specific design and materials, training pant 20 can have other designs or constructions.

Examples of other representative training pants are disclosed in U.S. Pat. No. 4,940,464, the contents of which are incorporated by reference herein, and U.S. Pat. No. 4,641,381, the contents of which are incorporated by reference herein.

Continuing to refer to FIGS. 1 and 2, a separate waist elastic system 60 is associated with chassis 22 about waist opening 30. Waist elastic system 60 includes an elongate sleeve member 62 defining therein an elongate passage 64, and an elongate elastic member 66. Elongate sleeve member 62 can be formed from one layer of material, such as a nonwoven liquid permeable material, by folding the material into a C-shape configuration comprising an outer surface 68 (FIG. 2) and an inner surface 70, which define elongate passage 64. Outer surface 68 and inner surface 70 can be joined together in any suitable manner, such as by adhesives 72. Adhesives 72 join only outer surface 68 and inner surface 70 together, and do not contact elongate elastic member 66, which is substantially freely movable in elongate passage 64.

Elongate sleeve member 62 is joined, such as by adhesives 74, to peripheral edge portion 58 (FIG. 2), such that the portion of sleeve member 62 containing elongate elastic member 66 extends outwardly beyond the end edge 59 of peripheral edge portion 58. Desirably, waist elastic system 60 is joined to only one of the layers comprising chassis 22, such as outer layer 50, for purposes that will be explained hereafter. Within elongate passage 64, elongate elastic member 66 has an outermost peripheral edge 76, and an innermost peripheral edge 78 that is spaced a selective distance from absorbent end edge 40. Although elongate elastic member 66 is illustrated in FIG. 2 as a single ribbon of elastic material, it may comprise a plurality of elastic ribbons or strands. In the case in which elongate elastic member 66 is a plurality of strands or ribbons, outermost peripheral edge 76 will correspond to the outermost peripheral edge of the outermost strand or ribbon, and innermost peripheral edge 78 will correspond to the innermost peripheral edge of the innermost strand or ribbon.

Since waist elastic system 60 is a separate structure from chassis 22, waist elastic system 60 can be made and constructed of any types of desired material independent of the materials of which chassis 22 is made. This provides increased flexibility in the design and construction of waist elastic system 60.

In one embodiment, hereinafter also referred to as Embodiment 1, of disposable absorbent training pant 20, outer cover layer 46 comprises an outer layer 50 made of a liquid permeable spunbond polypropylene web having a basis weight of about 20 grams per square meter, and an inner layer 52 made of a 0.0015 centimeter polyethylene film. Liner 48 can be made of the same material as outer layer 50 and made hydrophilic by treating it with a wettable agent, or can be made of a hydrophilic material. Absorbent structure 38 can comprise a uniform mixture of any suitable superabsorbent material and wood pulp fluff, with the mixture enclosed in a tissue wrap to maintain the integrity of the superabsorbent material and fluff. Sleeve member 62 can be made of a nonwoven web of bicomponent fibers in a side-by-side orientation, in which the fibers are present in the amount of about 50 percent polypropylene fibers to about 50 percent polyethylene fibers. Sleeve member 62 desirably has a basis weight of about 17 gsm, and is constructed in a C-fold configuration to have a width of about 2.38 centimeters (15/16 inch) and a relaxed length of about 73.66 centimeters (29 inches), i.e., a circumferential length of about 73.66 centimeters. Elastic member 66 is made of a natural rubber material, and has a thickness of about 7 mils, a width of about 0.79 centimeters (5/16 inch), and a relaxed circumferential length of about 28.58 centimeters (11.25 inches). One process of constructing a waist elastic system 60 includes providing two lengths of natural rubber having respective relaxed lengths of about 14.28 centimeters (5 5/8 inches) (one-half of the relaxed circumferential length) and two lengths of the above-described nonwoven web having respective relaxed lengths of about 36.83 centimeters (14.5 inches). Each natural rubber length has a width of 0.79 centimeters (5/16 inch), and each nonwoven web length has a width of about 4.83 centimeters (1.9 inches) (twice the C-fold configuration width of 15/16 inch). Both natural rubber lengths are extended about 36.83 centimeters (14.5 inches) and placed on a respective nonwoven web length having a length of about 36.83 centimeters, with the ends of each natural rubber length being joined to the ends of its respective nonwoven web length. Each nonwoven web length is C-folded over its respective natural rubber length. The two resulting composites, comprising a natural rubber length and a nonwoven web length, are joined at their ends to form a closed-loop elastic waistband, such as a waist elastic system 60. The composites can be joined together in a relaxed state or extended state. The closed-loop elastic waistband has, in its relaxed state, a circumferential length of about 73.66 centimeters (29 inches).

Elongate sleeve member 62 and elongate elastic member 66 also can be joined to chassis 22 at seams 34 at the same time front panel 24 and back panel 26 are joined to form seams 34. Thus, between seams 34 (FIG. 1), elastic member 66 is freely movable within passage 64.

Waist elastic system 60 provides the features of a substantially uniform low tension over a wide size range, a more comfortable fit, and improved ease of use, over repeated uses of training pant 20. A repeated use refers, for example, to the child pulling the pant down to go to the bathroom, or pulling the pant up. It has been discovered that this type of repeated use with current training pants results in a substantial loss of elasticity about waist opening 30. To address this loss of elasticity over repeated uses, current training pants incorporate the waist elastic with a relatively high tension for the purpose of compensating for this loss of elasticity over repeated use. However, this relatively high tension of the waist elastic results in an uncomfortable fit, redmarking, and/or difficulty in pulling the pant up or down, all of which are undesirable to both the child and the parent or caretaker.

Figure 7:
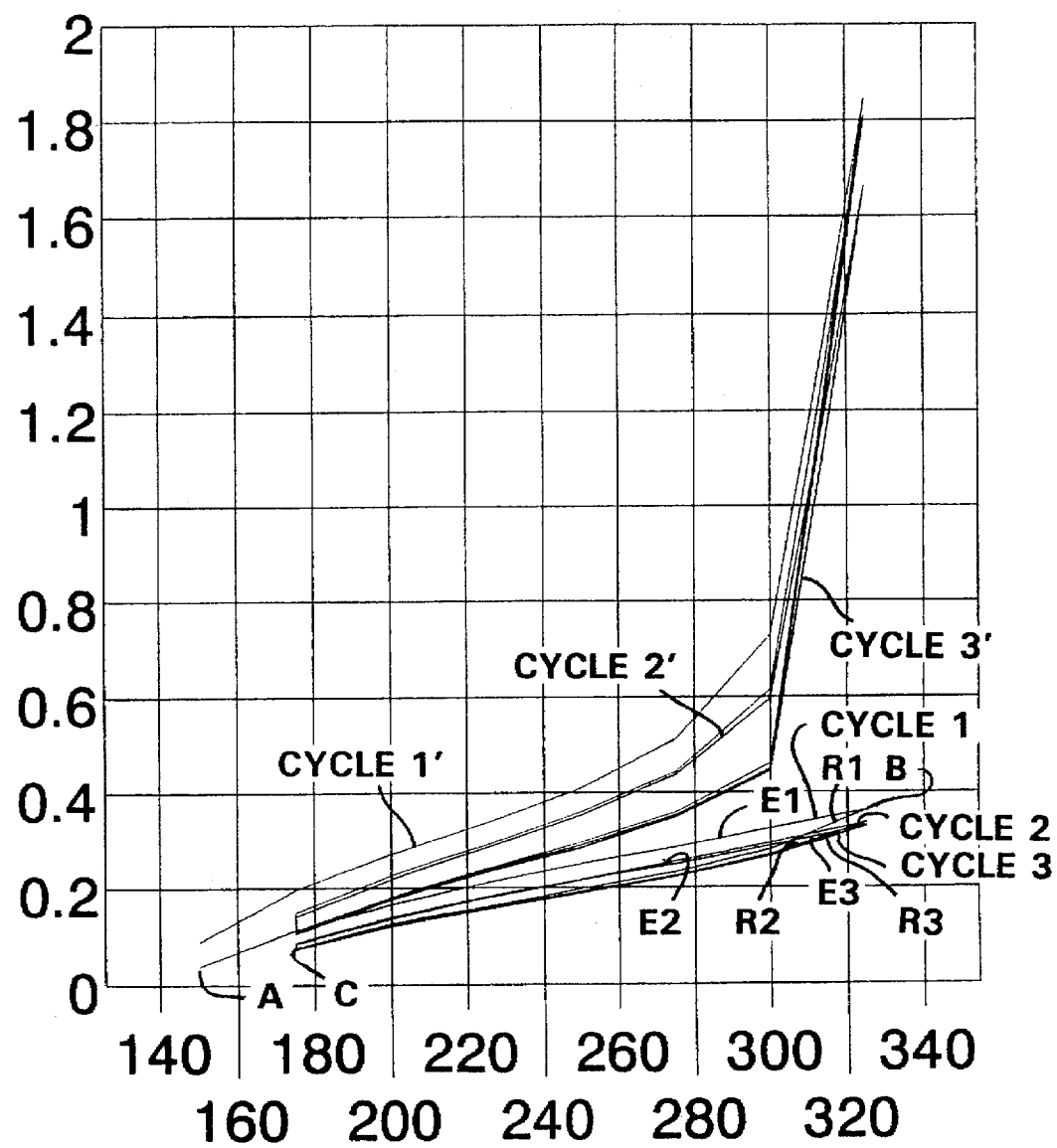
FIGS. 7–13 are graphs comparing the first three cycles of a training pant made in accordance with the principles of the present invention against the first three cycles of a current training pant product.
Figure 8:
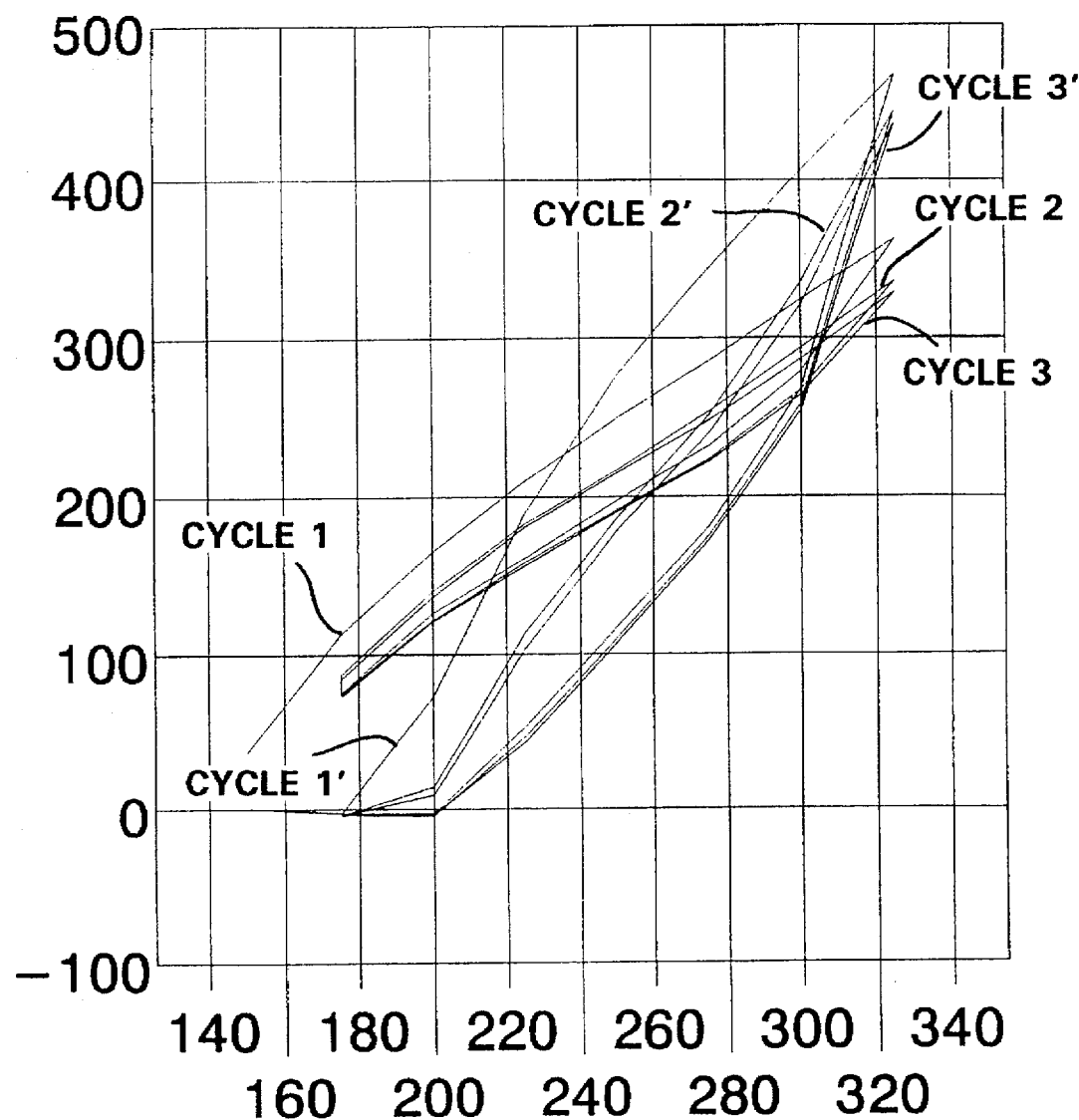

In analyzing this discovered problem, applicants have found that one important factor relating to these desired features is the average maximum rate of change of modulus of elasticity over the first three cycles, which will be described in greater detail below. FIGS. 7–13 compare the first three cycles of use of Embodiment 8 against a current training pant. A cycle represents one extension and one retraction of the waist elastic, which occurs generally when the child pulls the pant upwardly or pulls the pant downwardly. In FIG. 7, the first three cycles of Embodiment 1 are represented by the curves identified as cycle 1, cycle 2, and cycle 3. Cycle 1 comprises an extension E1 and a retraction R1, in which extension E1 begins at point A and ends at point B, and retraction R1 begins at point B and ends at point C. Each point A, B, and C represents a specific tension in grams at a specific extension in millimeters. Cycle 2 has an extension E2 and a retraction R2, and cycle 3 has an extension E3 and a retraction R3.

In comparison to the three cycles 1, 2, and 3 are the first three cycles 1', 2', and 3', of a current training pant, identified as Sample 1. When comparing cycles 1, 2, and 3 to cycles 1', 2', and 3' of Sample 1, the Sample 1 cycles 1', 2', and 3' have a much higher tension in grams over the extension range of 175 to 325 millimeters than cycles 1, 2, and 3. When taken over a range of extension of about 175–325 millimeters, Embodiment 1 provides a substantially more uniform, lower tension for the first three cycles than Sample 1.

FIGS. 8–13 are similar to FIG. 7, in that each of the FIGS. 8–13 compares the first three cycles 1, 2, and 3 of Embodiment 1 with the first three cycles 1', 2', and 3' of Samples 2–7, respectively. Note that the scales of the Y-axes, which represent the load or tension in grams, are different in FIGS. 7–13 in order to more clearly illustrate the comparisons.

Sample 1 (FIG. 7) was manufactured by The Drypers Corporation, is generally identified as Big Boy and Big Girl product, and was obtained from a product package having a bag count of 13 for boys and girls weighing up to 36 pounds.

Sample 2 (FIG. 8) was manufactured by Kimberly-Clark Corporation, is identified as HUGGIES® PULL-UPS® brand training pant product, and was obtained from a product package having a bag count of 16 for boys weighing 29–36 pounds and girls weighing 25–34 pounds.

Sample 3 (FIG. 9) was manufactured by Paragon Trade Brands, is generally identified as Kids Pants product, and was obtained from a product package having a bag count of 20 for boys and girls in the 24–33 pound weight range.

Sample 4 (FIG. 10) was manufactured by The Procter & Gamble Company, is generally identified as Pampers® Trainers® product, and was obtained from a product package having a bag count of 16 for boys and girls weighing 23–34 pounds.

Sample 5 (FIG. 11) was manufactured by Pope & Talbot, is generally sold through the Vons store chain, and was obtained from a product package having a bag count of 16 for boys and girls weighing 27–36 pounds.

Sample 6 (FIG. 12) was manufactured by Molnlycke Consumer Products AB, is generally identified as Libero Up & Go product, and was obtained from a product package having a bag count of 22 for boys and girls weighing 20–33 pounds (9–15 kilograms).

Sample 7 (FIG. 13) was manufactured by the Uni-Charm Corporation, is generally identified as Oyasumi Man product, and was obtained from a product package having a box count of 8 for boys and girls in the size range of 85–105 centimeters.

All products representing Samples 1–7 were commercially purchased in late 1994 or early 1995.

With regard to the description herein, a modulus of elasticity is a constant that numerically measures how much elasticity a material possesses, such as waist elastic system 60. A constant, with reference to FIG. 7, for example, is the slope represented by any two points on a curve of any one of the illustrated cycles. An average maximum rate of change of modulus of elasticity is calculated by averaging a selected number of slopes taken at specified points of a particular curve. Each curve of each cycle, and this includes the portion representing the extension and the portion representing the retraction in the cycle, had a slope calculated at every 25 millimeter increment within the extension range of 175 millimeters to 325 millimeters. The lower average slope, whether during an extension, a retraction, or a cycle, of Embodiment 1 in comparison to the higher average slope of any of the Samples 1–7, indicates a substantially lower rate of increase in tension over a wide size range than any of the Samples 1–7.

The average maximum rates of change of modulus of elasticity over the first three cycles are calculated from the data presented in Tables 1–9.

TABLE 1

EMBODIMENT 1
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | 104.57 | 120.15 | 122.37 | 102.35 | 115.70 | 113.03 | 2.10 |
|  | 200 | 155.75 | 171.32 | 178.00 | 149.07 | 173.55 | 165.54 | 1.78 |
|  | 225 | 198.02 | 213.60 | 220.27 | 198.02 | 220.27 | 210.04 | 1.58 |
|  | 250 | 235.85 | 251.42 | 262.55 | 233.62 | 264.77 | 249.64 | 1.42 |
|  | 275 | 267.00 | 289.24 | 300.37 | 267.00 | 302.59 | 285.24 | 1.53 |
|  | 300 | 302.59 | 329.29 | 342.64 | 300.37 | 342.64 | 323.51 | 1.55 |
|  | 325 | 340.42 | 371.57 | 382.69 | 335.97 | 380.47 | 362.22 |  |
| Retraction 1 | 325 | 340.42 | 371.57 | 382.69 | 335.97 | 380.47 | 362.22 | 3.33 |
|  | 300 | 264.77 | 278.12 | 284.80 | 267.00 | 300.37 | 279.01 | 1.87 |
|  | 275 | 220.27 | 231.40 | 238.07 | 220.27 | 251.42 | 232.29 | 1.41 |
|  | 250 | 186.90 | 195.80 | 200.25 | 189.12 | 213.60 | 197.13 | 1.44 |
|  | 225 | 149.07 | 160.20 | 166.87 | 151.30 | 178.00 | 161.09 | 1.39 |
|  | 200 | 115.70 | 126.82 | 133.50 | 120.15 | 135.72 | 126.38 | 2.05 |
|  | 175 | 68.97 | 77.87 | 77.87 | 68.97 | 82.32 | 75.20 |  |
| Extension 2 | 175 | 77.87 | 91.22 | 93.45 | 77.87 | 93.45 | 86.77 | 2.14 |
|  | 200 | 131.27 | 142.40 | 146.85 | 131.27 | 149.07 | 140.17 | 1.71 |
|  | 225 | 173.55 | 182.45 | 189.12 | 171.32 | 198.02 | 182.89 | 1.35 |
|  | 250 | 206.92 | 218.05 | 220.27 | 204.70 | 233.62 | 216.71 | 1.50 |
|  | 275 | 240.30 | 253.65 | 262.55 | 240.30 | 273.67 | 254.09 | 1.57 |
|  | 300 | 278.12 | 291.47 | 304.82 | 275.90 | 315.94 | 293.25 | 1.69 |
|  | 325 | 320.39 | 338.19 | 347.09 | 311.49 | 360.44 | 335.52 |  |
| Retraction 2 | 325 | 320.39 | 338.19 | 347.09 | 311.49 | 360.44 | 335.52 | 2.71 |
|  | 300 | 255.87 | 269.22 | 273.67 | 253.65 | 287.02 | 267.89 | 1.76 |
|  | 275 | 213.60 | 220.27 | 229.17 | 213.60 | 242.52 | 223.83 | 1.30 |

TABLE 1-continued

EMBODIMENT 1
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| | 250 | 180.22 | 191.35 | 195.80 | 182.45 | 206.92 | 191.35 | 1.32 |
| | 225 | 149.07 | 160.20 | 162.42 | 149.07 | 171.32 | 158.42 | 1.46 |
| | 200 | 113.47 | 122.37 | 126.82 | 115.70 | 131.27 | 121.93 | 1.90 |
| | 175 | 68.97 | 77.87 | 77.87 | 68.97 | 77.87 | 74.31 | |
| Extension 3 | 175 | 75.65 | 86.77 | 91.22 | 75.65 | 91.22 | 84.10 | 2.10 |
| | 200 | 126.82 | 137.95 | 140.17 | 129.05 | 149.07 | 136.61 | 1.76 |
| | 225 | 169.10 | 182.45 | 184.67 | 171.32 | 195.80 | 180.87 | 1.37 |
| | 250 | 202.47 | 215.82 | 220.27 | 204.70 | 231.40 | 214.93 | 1.33 |
| | 275 | 233.62 | 249.20 | 253.65 | 235.85 | 269.22 | 248.31 | 1.53 |
| | 300 | 271.45 | 289.24 | 293.69 | 271.45 | 307.04 | 286.58 | 1.67 |
| | 325 | 309.27 | 331.52 | 344.87 | 307.04 | 349.32 | 328.40 | |
| Retraction 3 | 325 | 309.27 | 331.52 | 344.87 | 307.04 | 349.32 | 328.40 | 2.56 |
| | 300 | 249.00 | 264.77 | 271.45 | 251.42 | 284.80 | 264.33 | 1.67 |
| | 275 | 211.37 | 218.05 | 229.17 | 213.60 | 240.30 | 222.50 | 1.30 |
| | 250 | 178.00 | 189.12 | 195.80 | 182.45 | 204.70 | 190.01 | 1.35 |
| | 225 | 146.85 | 153.52 | 162.42 | 149.07 | 169.10 | 156.19 | 1.41 |
| | 200 | 113.47 | 120.15 | 124.60 | 117.92 | 129.05 | 121.04 | 1.92 |
| | 175 | 66.75 | 75.65 | 75.65 | 68.97 | 77.87 | 72.98 | |

TABLE 2

EMBODIMENT 2
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | 133.50 | 113.47 | 104.57 | 122.37 | 106.80 | 116.14 | 2.37 |
| | 200 | 191.35 | 171.32 | 162.42 | 182.45 | 169.10 | 175.33 | 1.96 |
| | 225 | 238.07 | 220.27 | 209.15 | 233.62 | 220.27 | 224.28 | 1.85 |
| | 250 | 282.57 | 267.00 | 253.65 | 280.35 | 269.22 | 270.56 | 1.67 |
| | 275 | 324.84 | 307.04 | 291.47 | 322.62 | 315.94 | 312.38 | 1.80 |
| | 300 | 373.79 | 351.54 | 333.74 | 367.12 | 360.44 | 357.33 | 1.96 |
| | 325 | 418.29 | 402.72 | 378.24 | 420.52 | 411.62 | 406.28 | |
| Retraction 1 | 325 | 418.29 | 402.72 | 378.24 | 420.52 | 411.62 | 406.28 | 4.45 |
| | 300 | 302.59 | 291.47 | 282.57 | 307.04 | 291.47 | 295.03 | 2.08 |
| | 275 | 249.20 | 240.30 | 233.62 | 253.65 | 238.07 | 242.97 | 1.55 |
| | 250 | 211.37 | 202.47 | 193.57 | 215.82 | 198.02 | 204.25 | 1.55 |
| | 225 | 171.32 | 166.87 | 155.75 | 173.55 | 160.20 | 165.54 | 1.64 |
| | 200 | 131.27 | 126.82 | 115.70 | 131.27 | 117.92 | 124.60 | 2.10 |
| | 175 | 77.87 | 73.42 | 64.52 | 77.87 | 66.75 | 72.09 | |
| Extension 2 | 175 | 100.12 | 86.77 | 77.87 | 91.22 | 80.10 | 87.22 | 2.26 |
| | 200 | 149.07 | 144.62 | 135.72 | 149.07 | 140.17 | 143.73 | 1.83 |
| | 225 | 198.02 | 186.90 | 180.22 | 198.02 | 184.67 | 189.57 | 1.58 |
| | 250 | 238.07 | 224.72 | 220.27 | 240.30 | 222.50 | 229.17 | 1.60 |
| | 275 | 278.12 | 264.77 | 255.87 | 280.35 | 267.00 | 269.22 | 1.92 |
| | 300 | 327.07 | 315.94 | 298.14 | 329.29 | 315.94 | 317.28 | 1.94 |
| | 325 | 378.24 | 362.67 | 344.87 | 380.47 | 362.67 | 365.78 | |
| Retraction 2 | 325 | 378.24 | 362.67 | 344.87 | 380.47 | 362.67 | 365.78 | 3.31 |
| | 300 | 291.47 | 280.35 | 271.45 | 291.47 | 280.35 | 283.02 | 1.96 |
| | 275 | 240.30 | 231.40 | 222.50 | 244.75 | 231.40 | 234.07 | 1.44 |
| | 250 | 202.47 | 198.02 | 189.12 | 206.92 | 193.57 | 198.02 | 1.51 |
| | 225 | 166.87 | 162.42 | 149.07 | 169.10 | 153.52 | 160.20 | 1.57 |
| | 200 | 129.05 | 122.37 | 113.47 | 126.82 | 113.47 | 121.04 | 2.06 |
| | 175 | 75.65 | 71.20 | 62.30 | 73.42 | 64.52 | 69.42 | |
| Extension 3 | 175 | 93.45 | 84.55 | 75.85 | 86.77 | 75.65 | 83.21 | 2.31 |
| | 200 | 149.07 | 140.17 | 133.50 | 149.07 | 133.50 | 141.06 | 1.82 |
| | 225 | 193.57 | 182.45 | 175.77 | 198.02 | 182.45 | 186.45 | 1.51 |
| | 250 | 233.62 | 220.27 | 213.60 | 233.82 | 220.27 | 224.28 | 1.53 |
| | 275 | 271.45 | 260.32 | 246.97 | 275.90 | 258.10 | 262.55 | 1.85 |
| | 300 | 318.17 | 307.04 | 291.47 | 320.39 | 307.04 | 308.82 | 1.96 |
| | 325 | 364.89 | 360.44 | 335.97 | 369.34 | 358.22 | 357.77 | |
| Retraction 3 | 325 | 364.89 | 360.44 | 335.97 | 369.34 | 358.22 | 357.77 | 3.10 |
| | 300 | 287.02 | 278.12 | 269.22 | 291.47 | 275.90 | 280.35 | 1.87 |
| | 275 | 240.30 | 233.62 | 220.27 | 244.75 | 229.17 | 233.62 | 1.46 |
| | 250 | 202.47 | 195.80 | 189.12 | 206.92 | 191.35 | 197.13 | 1.53 |
| | 225 | 166.87 | 160.20 | 149.07 | 169.10 | 149.07 | 158.86 | 1.58 |
| | 200 | 126.82 | 122.37 | 109.02 | 124.60 | 113.47 | 119.26 | 2.10 |
| | 175 | 75.65 | 66.75 | 60.07 | 71.20 | 60.07 | 66.75 | |

TABLE 3

SAMPLE 1
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | 191.35 | 209.15 | 193.57 | 198.02 | 191.35 | 196.69 | 2.95 |
|  | 200 | 262.55 | 282.57 | 269.22 | 273.67 | 264.77 | 270.56 | 2.67 |
|  | 225 | 327.07 | 349.32 | 338.19 | 342.64 | 329.29 | 337.30 | 2.92 |
|  | 250 | 396.04 | 424.97 | 411.62 | 418.29 | 400.49 | 410.28 | 4.08 |
|  | 275 | 489.49 | 538.44 | 511.74 | 527.32 | 493.94 | 512.19 | 8.67 |
|  | 300 | 678.61 | 829.91 | 696.41 | 760.94 | 678.61 | 728.90 | 44.65 |
|  | 325 | 1677.62 | 2159.33 | 1635.35 | 2147.09 | 1606.42 | 1845.16 |  |
| Retraction 1 | 325 | 1677.62 | 2159.33 | 1635.35 | 2147.09 | 1606.42 | 1845.16 | 55.37 |
|  | 300 | 449.44 | 471.69 | 462.79 | 465.02 | 456.12 | 461.01 | 4.13 |
|  | 275 | 351.54 | 362.67 | 358.22 | 362.67 | 353.77 | 357.77 | 2.49 |
|  | 250 | 289.24 | 298.14 | 295.92 | 298.14 | 295.92 | 295.47 | 2.21 |
|  | 225 | 233.62 | 244.75 | 240.30 | 242.52 | 240.30 | 240.30 | 2.37 |
|  | 200 | 175.77 | 184.67 | 180.22 | 182.45 | 182.45 | 181.11 | 2.74 |
|  | 175 | 106.80 | 117.92 | 111.25 | 113.47 | 113.47 | 112.58 |  |
| Extension 2 | 175 | 146.85 | 155.75 | 146.85 | 149.07 | 151.30 | 149.96 | 3.03 |
|  | 200 | 222.50 | 231.40 | 224.72 | 224.72 | 224.72 | 225.61 | 2.60 |
|  | 225 | 284.80 | 295.92 | 291.47 | 295.92 | 284.80 | 290.58 | 2.74 |
|  | 250 | 351.54 | 367.12 | 358.22 | 364.89 | 353.77 | 359.11 | 3.38 |
|  | 275 | 431.64 | 453.89 | 444.99 | 453.89 | 433.87 | 443.66 | 6.87 |
|  | 300 | 589.61 | 638.56 | 616.31 | 634.11 | 598.51 | 615.42 | 47.83 |
|  | 325 | 1688.75 | 1824.47 | 1415.08 | 2296.18 | 1831.14 | 1811.12 |  |
| Retraction 2 | 325 | 1688.75 | 1824.47 | 1415.08 | 2296.16 | 1831.14 | 1811.12 | 54.45 |
|  | 300 | 440.54 | 456.12 | 451.67 | 453.89 | 447.22 | 449.89 | 3.93 |
|  | 275 | 347.09 | 353.77 | 351.54 | 353.77 | 351.54 | 351.54 | 2.47 |
|  | 250 | 282.57 | 291.47 | 291.47 | 291.47 | 291.47 | 289.69 | 2.14 |
|  | 225 | 231.40 | 238.07 | 235.85 | 238.07 | 238.07 | 236.29 | 2.33 |
|  | 200 | 173.55 | 180.22 | 175.77 | 178.00 | 182.45 | 178.00 | 2.76 |
|  | 175 | 104.57 | 115.70 | 106.80 | 106.80 | 111.25 | 109.02 |  |
| Extension 3 | 175 | 137.95 | 149.07 | 140.17 | 140.17 | 140.17 | 141.51 | 3.06 |
|  | 200 | 211.37 | 224.72 | 220.27 | 220.27 | 213.60 | 218.05 | 2.69 |
|  | 225 | 282.57 | 287.02 | 282.57 | 291.47 | 282.57 | 285.24 | 2.69 |
|  | 250 | 349.32 | 353.77 | 353.77 | 353.77 | 351.54 | 352.43 | 3.44 |
|  | 275 | 431.64 | 449.44 | 436.09 | 442.77 | 431.64 | 438.32 | 6.34 |
|  | 300 | 574.04 | 614.09 | 596.29 | 614.09 | 585.16 | 596.73 | 42.69 |
|  | 325 | 1639.80 | 1688.75 | 1363.90 | 2239.42 | 1388.38 | 1664.05 |  |
| Retraction 3 | 325 | 1639.80 | 1688.75 | 1363.90 | 2239.42 | 1388.38 | 1664.05 | 48.76 |
|  | 300 | 436.09 | 449.44 | 447.22 | 449.44 | 442.77 | 444.99 | 3.84 |
|  | 275 | 344.87 | 349.32 | 349.32 | 351.54 | 349.32 | 348.87 | 2.58 |
|  | 250 | 282.57 | 284.80 | 284.80 | 282.57 | 287.02 | 284.35 | 2.05 |
|  | 225 | 226.95 | 235.85 | 233.62 | 233.62 | 235.85 | 233.18 | 2.30 |
|  | 200 | 169.10 | 178.00 | 175.77 | 175.77 | 180.22 | 175.77 | 2.79 |
|  | 175 | 102.35 | 111.25 | 102.35 | 104.57 | 109.02 | 105.91 |  |

TABLE 4

SAMPLE 2
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | −4.45 | −2.22 | −2.22 | −2.22 | −2.22 | −2.67 | 3.03 |
|  | 200 | 71.18 | 73.41 | 82.31 | 68.96 | 68.96 | 72.96 | 4.66 |
|  | 225 | 182.41 | 189.08 | 200.20 | 180.18 | 195.75 | 189.53 | 3.47 |
|  | 250 | 264.71 | 278.06 | 286.96 | 262.49 | 289.18 | 276.28 | 2.67 |
|  | 275 | 322.55 | 349.24 | 351.47 | 327.00 | 364.81 | 343.01 | 2.51 |
|  | 300 | 375.94 | 415.98 | 413.75 | 384.83 | 438.22 | 405.75 | 2.51 |
|  | 325 | 436.00 | 476.04 | 480.49 | 444.90 | 504.96 | 468.48 |  |
| Retraction 1 | 325 | 436.00 | 476.04 | 480.49 | 444.90 | 504.96 | 468.48 | 8.01 |
|  | 300 | 242.47 | 275.84 | 275.84 | 255.82 | 291.41 | 268.27 | 3.51 |
|  | 275 | 160.16 | 186.86 | 184.63 | 173.51 | 197.98 | 180.63 | 2.54 |
|  | 250 | 102.33 | 122.35 | 120.12 | 113.45 | 126.80 | 117.01 | 2.54 |
|  | 225 | 44.49 | 55.61 | 57.84 | 53.39 | 55.61 | 53.39 | 2.24 |
|  | 200 | −8.90 | −2.22 | 0.00 | 0.00 | −2.22 | −2.67 | 0.04 |
|  | 175 | −11.12 | −2.22 | −2.22 | −2.22 | 0.00 | −3.56 |  |
| Extension 2 | 175 | −11.12 | −2.22 | −2.22 | −2.22 | −2.22 | −4.00 | 0.75 |
|  | 200 | 11.12 | 15.57 | 17.80 | 15.57 | 13.35 | 14.88 | 3.97 |
|  | 225 | 97.88 | 117.90 | 122.35 | 106.78 | 124.57 | 113.89 | 2.88 |
|  | 250 | 164.61 | 193.53 | 189.08 | 180.18 | 202.43 | 185.97 | 2.62 |
|  | 275 | 226.90 | 258.04 | 255.82 | 242.47 | 273.61 | 251.37 | 3.31 |
|  | 300 | 304.75 | 342.57 | 340.35 | 320.33 | 362.59 | 334.12 | 4.43 |
|  | 325 | 422.65 | 444.90 | 447.12 | 436.00 | 473.81 | 444.90 |  |

TABLE 4-continued

SAMPLE 2
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Retraction 2 | 325 | 422.65 | 444.90 | 447.12 | 436.00 | 473.81 | 444.90 | 7.44 |
|  | 300 | 233.57 | 266.94 | 264.71 | 249.14 | 280.28 | 258.93 | 3.36 |
|  | 275 | 155.71 | 180.18 | 177.96 | 169.06 | 191.31 | 174.84 | 2.60 |
|  | 250 | 95.65 | 113.45 | 113.45 | 106.78 | 120.12 | 109.89 | 2.51 |
|  | 225 | 37.82 | 48.94 | 51.16 | 46.71 | 51.16 | 47.16 | 2.05 |
|  | 200 | −11.12 | −2.22 | −2.22 | −2.22 | −2.22 | −4.00 | −0.02 |
|  | 175 | −11.12 | −2.22 | 0.00 | −2.22 | −2.22 | −3.56 |  |
| Extension 3 | 175 | 11.12 | −2.22 | −2.22 | −2.22 | −2.22 | −4.00 | 0.53 |
|  | 200 | 2.22 | 8.90 | 17.80 | 11.12 | 6.67 | 9.34 | 3.75 |
|  | 225 | 88.98 | 109.00 | 111.22 | 97.88 | 109.00 | 103.22 | 2.99 |
|  | 250 | 160.16 | 182.41 | 182.41 | 171.28 | 193.53 | 177.96 | 2.47 |
|  | 275 | 215.77 | 246.92 | 244.69 | 229.12 | 262.49 | 239.80 | 3.22 |
|  | 300 | 291.41 | 327.00 | 327.00 | 306.98 | 349.24 | 320.33 | 4.66 |
|  | 325 | 411.53 | 431.55 | 436.00 | 424.88 | 480.49 | 436.89 |  |
| Retraction 3 | 325 | 411.53 | 431.55 | 436.00 | 424.88 | 480.49 | 436.89 | 7.28 |
|  | 300 | 229.12 | 262.49 | 260.26 | 244.69 | 278.06 | 254.93 | 3.31 |
|  | 275 | 151.26 | 177.96 | 175.73 | 166.84 | 189.08 | 172.17 | 2.60 |
|  | 250 | 91.20 | 111.22 | 111.22 | 104.55 | 117.90 | 107.22 | 2.54 |
|  | 225 | 35.59 | 44.49 | 46.71 | 44.49 | 46.71 | 43.60 | 1.89 |
|  | 200 | −11.12 | −2.22 | −2.22 | −2.22 | 0.00 | −3.56 | −0.02 |
|  | 175 | −11.12 | 0.00 | −2.22 | −2.22 | 0.00 | −3.11 |  |

TABLE 5

SAMPLE 3
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | 422.55 | 447.12 | 453.79 | 380.39 | 358.14 | 412.42 | 7.76 |
|  | 200 | 627.30 | 654.00 | 665.12 | 553.90 | 531.65 | 606.39 | 7.55 |
|  | 225 | 838.63 | 851.98 | 856.42 | 718.51 | 709.61 | 795.03 | 9.13 |
|  | 250 | 1094.44 | 1098.89 | 1096.67 | 909.81 | 916.49 | 1023.26 | 11.66 |
|  | 275 | 1412.54 | 1421.44 | 1410.32 | 1161.18 | 1167.85 | 1314.67 | 15.70 |
|  | 300 | 1825.19 | 1851.88 | 1822.96 | 1523.77 | 1512.65 | 1707.29 | 19.81 |
|  | 325 | 2335.70 | 2365.73 | 2327.92 | 1995.36 | 1987.57 | 2202.46 |  |
| Retraction 1 | 325 | 2335.70 | 2365.73 | 2327.92 | 1995.36 | 1987.57 | 2202.46 | 50.73 |
|  | 300 | 947.63 | 994.34 | 989.89 | 860.87 | 878.67 | 934.28 | 13.79 |
|  | 275 | 587.26 | 636.20 | 625.08 | 540.55 | 558.34 | 589.49 | 7.67 |
|  | 250 | 395.96 | 431.55 | 424.88 | 362.59 | 373.71 | 397.74 | 5.50 |
|  | 225 | 258.04 | 286.96 | 282.51 | 233.57 | 240.24 | 260.26 | 4.63 |
|  | 200 | 144.59 | 164.61 | 164.61 | 124.57 | 124.57 | 144.59 | 4.00 |
|  | 175 | 48.94 | 60.06 | 57.84 | 28.92 | 26.69 | 44.49 |  |
| Extension 2 | 175 | 164.61 | 173.51 | 180.18 | 126.80 | 126.80 | 154.38 | 6.10 |
|  | 200 | 315.88 | 333.67 | 331.45 | 273.61 | 280.28 | 306.98 | 5.82 |
|  | 225 | 462.69 | 496.06 | 480.49 | 404.86 | 418.20 | 452.46 | 6.92 |
|  | 250 | 631.75 | 676.24 | 669.57 | 571.69 | 578.36 | 625.52 | 9.72 |
|  | 275 | 874.22 | 932.06 | 925.38 | 791.91 | 818.81 | 868.44 | 16.19 |
|  | 300 | 1296.87 | 1363.61 | 1354.71 | 1161.18 | 1190.10 | 1273.29 | 28.15 |
|  | 325 | 2044.30 | 2106.58 | 2064.32 | 1772.91 | 1897.48 | 1977.12 |  |
| Retraction 2 | 325 | 2044.30 | 2106.58 | 2064.32 | 1772.91 | 1897.48 | 1977.12 | 43.48 |
|  | 300 | 896.47 | 949.85 | 940.95 | 820.83 | 843.08 | 890.24 | 12.94 |
|  | 275 | 562.79 | 611.73 | 602.83 | 518.30 | 538.32 | 566.80 | 7.46 |
|  | 250 | 378.16 | 413.75 | 411.53 | 342.57 | 355.92 | 380.39 | 5.30 |
|  | 225 | 246.92 | 273.61 | 271.39 | 220.22 | 226.90 | 247.81 | 4.64 |
|  | 200 | 133.47 | 149.04 | 155.71 | 109.00 | 111.22 | 131.69 | 3.95 |
|  | 175 | 35.59 | 46.71 | 44.49 | 17.80 | 20.02 | 32.92 |  |
| Extension 3 | 175 | 140.14 | 155.71 | 160.16 | 106.78 | 109.00 | 134.36 | 6.26 |
|  | 200 | 291.41 | 313.65 | 322.55 | 264.71 | 262.49 | 290.96 | 5.64 |
|  | 225 | 431.55 | 471.59 | 462.69 | 395.96 | 398.18 | 431.99 | 6.64 |
|  | 250 | 605.06 | 642.87 | 633.98 | 542.77 | 565.02 | 597.94 | 9.08 |
|  | 275 | 840.95 | 880.89 | 872.00 | 751.87 | 778.57 | 824.84 | 15.13 |
|  | 300 | 1241.26 | 1283.52 | 1267.95 | 1094.44 | 1127.81 | 1203.00 | 28.09 |
|  | 325 | 1936.41 | 2002.03 | 1951.98 | 1814.06 | 1821.85 | 1905.27 |  |
| Retraction 3 | 325 | 1936.41 | 2002.03 | 1951.98 | 1814.06 | 1821.85 | 1905.27 | 41.51 |
|  | 300 | 865.32 | 927.61 | 914.26 | 803.04 | 827.51 | 867.55 | 12.47 |
|  | 275 | 551.67 | 598.38 | 587.26 | 511.63 | 529.43 | 555.67 | 7.39 |
|  | 250 | 367.04 | 404.86 | 395.96 | 338.12 | 349.24 | 371.04 | 5.27 |
|  | 225 | 238.02 | 264.71 | 260.26 | 215.77 | 218.00 | 239.35 | 4.59 |

TABLE 5-continued

SAMPLE 3
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| | 200 | 124.57 | 144.59 | 142.37 | 104.55 | 106.78 | 124.57 | 3.83 |
| | 175 | 31.14 | 44.49 | 40.04 | 15.57 | 13.35 | 28.92 | |

TABLE 6

SAMPLE 4
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | −2.22 | −2.22 | −4.45 | 2.22 | −2−22 | −1.78 | 5.58 |
| | 200 | 128.91 | 153.36 | 128.91 | 148.91 | 128.91 | 137.80 | 8.05 |
| | 225 | 322.27 | 342.27 | 340.05 | 353.39 | 337.83 | 339.16 | 6.17 |
| | 250 | 473.40 | 484.52 | 502.30 | 513.41 | 493.41 | 493.41 | 5.32 |
| | 275 | 602.31 | 602.31 | 644.54 | 657.88 | 624.54 | 626.32 | 5.39 |
| | 300 | 742.33 | 731.22 | 782.34 | 793.45 | 755.67 | 761.00 | 4.57 |
| | 325 | 860.13 | 840.13 | 886.80 | 915.69 | 873.46 | 875.24 | |
| Retraction 1 | 325 | 860.13 | 840.13 | 886.80 | 915.69 | 873.46 | 875.24 | 12.18 |
| | 300 | 557.86 | 560.08 | 575.64 | 586.75 | 573.42 | 570.75 | 6.49 |
| | 275 | 400.06 | 404.50 | 411.17 | 420.06 | 406.73 | 408.51 | 5.57 |
| | 250 | 262.26 | 271.15 | 268.93 | 277.82 | 266.71 | 269.37 | 5.49 |
| | 225 | 128.91 | 140.02 | 128.91 | 135.58 | 126.69 | 132.02 | 4.98 |
| | 200 | 4.45 | 13.34 | 2.22 | 13.34 | 4.45 | 7.56 | 0.48 |
| | 175 | −4.45 | −4.45 | −4.45 | −4.45 | −4.45 | −4.45 | |
| Extension 2 | 175 | −4.45 | −4.45 | −4.45 | −4.45 | −4.45 | −4.45 | 2.08 |
| | 200 | 42.23 | 62.23 | 37.78 | 51.12 | 44.45 | 47.56 | 7.11 |
| | 225 | 215.59 | 233.37 | 220.03 | 228.92 | 228.92 | 225.37 | 5.97 |
| | 250 | 371.17 | 373.39 | 368.94 | 386.72 | 373.39 | 374.72 | 5.42 |
| | 275 | 500.07 | 506.74 | 513.41 | 522.30 | 508.96 | 510.30 | 5.87 |
| | 300 | 644.54 | 642.32 | 662.32 | 677.88 | 657.88 | 656.99 | 6.85 |
| | 325 | 806.79 | 793.45 | 826.79 | 849.02 | 840.13 | 823.23 | |
| Retraction 2 | 325 | 806.79 | 793.45 | 826.79 | 849.02 | 840.13 | 823.23 | 10.92 |
| | 300 | 537.86 | 551.19 | 553.42 | 562.31 | 546.75 | 550.30 | 6.37 |
| | 275 | 384.50 | 388.95 | 393.39 | 397.84 | 391.17 | 391.17 | 5.44 |
| | 250 | 248.93 | 257.82 | 255.59 | 262.26 | 251.15 | 255.15 | 5.41 |
| | 225 | 117.80 | 126.69 | 117.80 | 124.46 | 113.35 | 120.02 | 4.69 |
| | 200 | 0.00 | 6.67 | 0.00 | 8.89 | −2.22 | 2.67 | 0.20 |
| | 175 | −2.22 | −2.22 | −2.22 | −2.22 | −2.22 | −2.22 | |
| Extension 3 | 175 | −4.45 | −4.45 | −4.45 | −4.45 | −4.45 | −4.45 | 1.51 |
| | 200 | 33.34 | 46.67 | 24.45 | 40.01 | 22.23 | 33.34 | 7.25 |
| | 225 | 204.47 | 228.92 | 204.47 | 224.48 | 211.14 | 214.70 | 5.80 |
| | 250 | 346.72 | 364.50 | 360.05 | 368.94 | 357.83 | 359.61 | 5.21 |
| | 275 | 482.29 | 486.74 | 493.41 | 500.07 | 486.74 | 489.85 | 5.71 |
| | 300 | 624.54 | 622.31 | 635.65 | 648.99 | 631.21 | 632.54 | 6.70 |
| | 325 | 784.56 | 800.12 | 802.34 | 822.34 | 791.23 | 800.12 | |
| Retraction 3 | 325 | 784.56 | 800.12 | 802.34 | 822.34 | 791.23 | 800.12 | 10.49 |
| | 300 | 531.19 | 528.97 | 542.30 | 551.19 | 535.64 | 537.86 | 6.15 |
| | 275 | 377.83 | 382.28 | 384.50 | 393.39 | 382.28 | 384.06 | 5.41 |
| | 250 | 244.48 | 248.93 | 248.93 | 257.82 | 244.48 | 248.93 | 5.35 |
| | 225 | 113.35 | 122.24 | 111.13 | 120.02 | 108.91 | 115.13 | 4.59 |
| | 200 | 0.00 | 2.22 | −4.45 | 6.67 | −2.22 | 0.44 | 0.12 |
| | 175 | −4.45 | −2.22 | −2.22 | −2.22 | −2.22 | −2.67 | |

TABLE 7

SAMPLE 5
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | 229.17 | 253.65 | 238.07 | 242.52 | 229.17 | 238.52 | 2.63 |
| | 200 | 298.14 | 318.17 | 307.04 | 304.82 | 293.69 | 304.37 | 2.55 |
| | 225 | 362.67 | 380.47 | 376.02 | 367.12 | 353.77 | 368.01 | 3.10 |
| | 250 | 438.32 | 458.34 | 456.12 | 440.54 | 433.87 | 445.44 | 4.33 |
| | 275 | 542.89 | 565.14 | 571.82 | 545.12 | 542.89 | 553.57 | 8.37 |
| | 300 | 734.24 | 772.06 | 814.34 | 736.46 | 756.49 | 762.72 | 36.07 |
| | 325 | 1588.62 | 1706.55 | 1775.52 | 1461.80 | 1789.98 | 1664.49 | |
| Retraction 1 | 325 | 1588.62 | 1706.55 | 1775.52 | 1461.80 | 1789.98 | 1664.49 | 48.25 |
| | 300 | 462.79 | 469.47 | 451.67 | 449.44 | 458.34 | 458.34 | 4.86 |

TABLE 7-continued

SAMPLE 5
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| | 275 | 340.42 | 347.09 | 331.52 | 331.52 | 333.74 | 336.86 | 2.35 |
| | 250 | 282.57 | 284.80 | 273.67 | 273.67 | 275.90 | 278.12 | 1.57 |
| | 225 | 242.52 | 246.97 | 233.62 | 235.85 | 235.85 | 238.96 | 1.57 |
| | 200 | 202.47 | 209.15 | 193.57 | 198.02 | 195.80 | 199.80 | 1.99 |
| | 175 | 151.30 | 164.65 | 140.17 | 149.07 | 144.62 | 149.96 | |
| Extension 2 | 175 | 186.90 | 198.02 | 178.00 | 182.45 | 180.22 | 185.12 | 2.63 |
| | 200 | 253.65 | 262.55 | 244.75 | 249.20 | 244.75 | 250.98 | 2.58 |
| | 225 | 315.94 | 324.84 | 309.27 | 315.94 | 311.49 | 315.50 | 2.88 |
| | 250 | 387.14 | 393.82 | 387.14 | 387.14 | 382.69 | 387.59 | 3.77 |
| | 275 | 473.92 | 496.17 | 482.82 | 478.37 | 478.37 | 481.93 | 7.01 |
| | 300 | 636.34 | 671.94 | 665.26 | 649.69 | 663.04 | 657.25 | 33.09 |
| | 325 | 1441.78 | 1530.77 | 1528.55 | 1314.95 | 1606.42 | 1484.49 | |
| Retraction 2 | 325 | 1441.78 | 1530.77 | 1528.55 | 1314.95 | 1606.42 | 1484.49 | 41.72 |
| | 300 | 444.99 | 451.67 | 438.32 | 433.87 | 438.32 | 441.43 | 4.54 |
| | 275 | 331.52 | 338.19 | 324.84 | 322.62 | 322.62 | 327.96 | 2.22 |
| | 250 | 275.90 | 280.35 | 269.22 | 269.22 | 267.00 | 272.34 | 1.58 |
| | 225 | 233.62 | 242.52 | 229.17 | 231.40 | 226.95 | 232.73 | 1.60 |
| | 200 | 195.80 | 202.47 | 186.90 | 191.35 | 186.90 | 192.68 | 1.98 |
| | 175 | 140.17 | 157.97 | 137.95 | 140.17 | 140.17 | 143.29 | |
| Extension 3 | 175 | 175.77 | 191.35 | 169.10 | 182.45 | 171.32 | 178.00 | 2.67 |
| | 200 | 244.75 | 255.87 | 238.07 | 246.97 | 238.07 | 244.75 | 2.47 |
| | 225 | 307.04 | 315.94 | 304.82 | 307.04 | 298.14 | 306.60 | 2.87 |
| | 250 | 380.47 | 391.59 | 373.79 | 376.02 | 369.34 | 378.24 | 3.68 |
| | 275 | 471.69 | 480.59 | 467.24 | 465.02 | 467.24 | 470.36 | 6.64 |
| | 300 | 634.11 | 649.69 | 634.11 | 622.99 | 640.79 | 636.34 | 36.65 |
| | 325 | 1753.27 | 1464.02 | 1419.53 | 1590.85 | 1535.22 | 1552.58 | |
| Retraction 3 | 325 | 1753.27 | 1464.02 | 1419.53 | 1590.85 | 1535.22 | 1552.58 | 44.62 |
| | 300 | 442.77 | 449.44 | 433.87 | 424.97 | 433.87 | 436.98 | 4.45 |
| | 275 | 333.74 | 335.97 | 320.39 | 318.17 | 320.39 | 325.73 | 2.24 |
| | 250 | 275.90 | 278.12 | 264.77 | 264.77 | 264.77 | 269.67 | 1.53 |
| | 225 | 235.85 | 240.30 | 224.72 | 229.17 | 226.95 | 231.40 | 1.60 |
| | 200 | 193.57 | 202.47 | 184.67 | 189.12 | 186.90 | 191.35 | 2.05 |
| | 175 | 137.95 | 155.75 | 131.27 | 137.95 | 137.95 | 140.17 | |

TABLE 8

SAMPLE 6
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | 220.22 | 202.43 | 231.35 | 218.00 | 213.55 | 217.11 | 4.18 |
| | 200 | 327.00 | 304.75 | 338.12 | 322.55 | 315.88 | 321.66 | 3.67 |
| | 225 | 422.65 | 395.96 | 429.32 | 415.98 | 402.63 | 413.31 | 3.74 |
| | 250 | 520.53 | 487.16 | 527.20 | 507.18 | 491.61 | 506.74 | 4.36 |
| | 275 | 636.20 | 591.71 | 638.43 | 618.41 | 593.94 | 615.74 | 6.48 |
| | 300 | 809.71 | 747.43 | 803.04 | 780.79 | 747.43 | 777.68 | 16.75 |
| | 325 | 1290.20 | 1145.61 | 1221.24 | 1212.34 | 1112.24 | 1196.33 | |
| Retraction 1 | 325 | 1290.20 | 1145.61 | 1221.24 | 1212.34 | 1112.24 | 1196.33 | 23.08 |
| | 300 | 633.98 | 602.83 | 636.20 | 620.63 | 602.83 | 619.30 | 5.00 |
| | 275 | 502.73 | 480.49 | 509.41 | 496.06 | 482.71 | 494.28 | 3.59 |
| | 250 | 411.53 | 391.51 | 418.20 | 407.08 | 393.73 | 404.41 | 3.24 |
| | 225 | 327.00 | 311.43 | 338.12 | 324.77 | 315.88 | 323.44 | 3.47 |
| | 200 | 238.02 | 224.67 | 251.37 | 235.79 | 233.57 | 236.68 | 4.02 |
| | 175 | 133.47 | 124.57 | 149.04 | 133.47 | 140.14 | 136.14 | |
| Extension 2 | 175 | 173.51 | 160.16 | 182.41 | 169.06 | 171.28 | 171.28 | 4.25 |
| | 200 | 282.51 | 264.71 | 289.18 | 278.06 | 273.61 | 277.62 | 3.61 |
| | 225 | 371.49 | 353.69 | 387.06 | 369.26 | 358.14 | 367.93 | 3.65 |
| | 250 | 462.69 | 440.45 | 476.04 | 464.92 | 451.57 | 459.13 | 4.18 |
| | 275 | 573.92 | 547.22 | 580.59 | 567.24 | 549.45 | 563.68 | 6.05 |
| | 300 | 734.08 | 694.04 | 731.85 | 720.73 | 694.04 | 714.95 | 18.88 |
| | 325 | 1339.14 | 1045.51 | 1285.75 | 1103.34 | 1161.18 | 1186.98 | |
| Retraction 2 | 325 | 1339.14 | 1045.51 | 1285.75 | 1103.34 | 1161.18 | 1186.98 | 23.19 |
| | 300 | 618.41 | 591.71 | 622.85 | 611.73 | 591.71 | 607.28 | 4.84 |
| | 275 | 496.06 | 471.59 | 500.51 | 487.16 | 476.04 | 486.27 | 3.49 |
| | 250 | 404.86 | 387.06 | 413.75 | 400.41 | 389.28 | 399.07 | 3.24 |
| | 225 | 320.33 | 306.98 | 331.45 | 320.33 | 311.43 | 318.10 | 3.47 |
| | 200 | 231.35 | 220.22 | 244.69 | 231.35 | 229.12 | 231.35 | 4.02 |
| | 175 | 129.02 | 120.12 | 142.37 | 129.02 | 133.47 | 130.80 | |
| Extension 3 | 175 | 164.61 | 153.49 | 177.96 | 162.39 | 166.84 | 165.06 | 4.31 |
| | 200 | 271.39 | 258.04 | 289.18 | 278.06 | 266.94 | 272.72 | 3.58 |

TABLE 8-continued

SAMPLE 6
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| | 225 | 364.81 | 344.79 | 380.39 | 367.04 | 353.69 | 362.15 | 3.68 |
| | 250 | 460.47 | 440.45 | 469.37 | 456.02 | 444.90 | 454.24 | 3.97 |
| | 275 | 565.02 | 538.32 | 567.24 | 556.12 | 540.55 | 553.45 | 5.84 |
| | 300 | 716.28 | 678.47 | 718.51 | 702.94 | 680.69 | 699.38 | 17.19 |
| | 325 | 1118.91 | 1012.14 | 1263.50 | 1243.48 | 1007.69 | 1129.15 | |
| Retraction 3 | 325 | 1118.91 | 1012.14 | 1263.50 | 1243.48 | 1007.69 | 1129.15 | 21.05 |
| | 300 | 613.96 | 585.04 | 618.41 | 605.06 | 591.71 | 602.83 | 4.84 |
| | 275 | 487.16 | 469.37 | 496.06 | 484.94 | 471.59 | 481.82 | 3.45 |
| | 250 | 400.41 | 382.61 | 409.30 | 398.18 | 387.06 | 395.51 | 3.19 |
| | 225 | 320.33 | 302.53 | 329.22 | 315.88 | 311.43 | 315.88 | 3.49 |
| | 200 | 229.12 | 218.00 | 240.24 | 229.12 | 226.90 | 228.68 | 4.00 |
| | 175 | 126.80 | 115.67 | 140.14 | 126.80 | 133.47 | 128.57 | |

TABLE 9

SAMPLE 7
TENSION (grams)

| Extension/Retraction | (mm) | Specimen 1 | Specimen 2 | Specimen 3 | Specimen 4 | Specimen 5 | Average (g) | Slope (g/mm) |
|---|---|---|---|---|---|---|---|---|
| Extension 1 | 175 | 129.17 | 133.63 | 120.27 | 104.68 | 89.09 | 115.37 | 3.55 |
| | 200 | 213.80 | 227.17 | 211.58 | 189.31 | 178.17 | 204.01 | 2.90 |
| | 225 | 291.75 | 300.66 | 291.75 | 256.12 | 242.76 | 276.61 | 2.87 |
| | 250 | 367.48 | 371.93 | 371.93 | 322.93 | 307.34 | 348.32 | 3.47 |
| | 275 | 463.24 | 458.79 | 467.70 | 398.66 | 387.52 | 435.18 | 7.93 |
| | 300 | 708.23 | 652.55 | 677.05 | 572.37 | 556.78 | 633.40 | 17.46 |
| | 325 | 1080.16 | 1097.98 | 1126.93 | 1035.62 | 1008.89 | 1069.91 | |
| Retraction 1 | 325 | 1080.16 | 1097.98 | 1126.93 | 1035.62 | 1008.89 | 1069.91 | 25.60 |
| | 300 | 474.38 | 454.34 | 454.34 | 385.29 | 380.84 | 429.84 | 4.13 |
| | 275 | 342.98 | 354.11 | 349.66 | 296.21 | 289.53 | 326.50 | 2.58 |
| | 250 | 273.94 | 287.30 | 280.62 | 238.30 | 229.39 | 261.91 | 2.48 |
| | 225 | 209.35 | 222.71 | 216.03 | 180.40 | 171.49 | 200.00 | 2.80 |
| | 200 | 135.86 | 151.45 | 140.31 | 118.04 | 104.68 | 130.06 | 3.40 |
| | 175 | 51.22 | 64.59 | 46.77 | 40.09 | 22.27 | 44.99 | |
| Extension 2 | 175 | 86.86 | 95.77 | 73.50 | 69.04 | 46.77 | 74.39 | 3.85 |
| | 200 | 182.62 | 191.53 | 178.17 | 158.13 | 142.54 | 170.60 | 2.89 |
| | 225 | 258.35 | 265.03 | 256.12 | 222.71 | 211.58 | 242.76 | 2.87 |
| | 250 | 329.62 | 342.98 | 331.84 | 291.75 | 276.16 | 314.47 | 3.24 |
| | 275 | 412.02 | 423.16 | 420.93 | 365.25 | 356.34 | 395.54 | 7.50 |
| | 300 | 657.00 | 603.55 | 612.46 | 525.60 | 516.69 | 583.06 | 18.26 |
| | 325 | 1028.94 | 1055.66 | 1075.71 | 1066.80 | 971.03 | 1039.63 | |
| Retraction 2 | 325 | 1028.94 | 1055.66 | 1075.71 | 1066.80 | 971.03 | 1039.63 | 24.85 |
| | 300 | 458.79 | 443.20 | 440.97 | 376.39 | 371.93 | 418.26 | 3.88 |
| | 275 | 338.52 | 347.43 | 342.98 | 291.75 | 285.07 | 321.15 | 2.55 |
| | 250 | 271.71 | 282.85 | 276.16 | 231.62 | 224.94 | 257.46 | 2.39 |
| | 225 | 209.35 | 218.26 | 213.80 | 178.17 | 169.26 | 197.77 | 2.90 |
| | 200 | 133.53 | 146.99 | 133.63 | 111.36 | 100.22 | 125.16 | 3.40 |
| | 175 | 49.00 | 57.91 | 42.32 | 33.41 | 17.82 | 40.09 | |
| Extension 3 | 175 | 77.95 | 91.31 | 66.81 | 62.36 | 40.09 | 67.70 | 3.90 |
| | 200 | 173.72 | 184.85 | 171.49 | 153.67 | 142.54 | 165.25 | 3.08 |
| | 225 | 253.89 | 265.03 | 256.12 | 222.71 | 213.80 | 242.31 | 2.69 |
| | 250 | 325.16 | 334.07 | 329.62 | 285.07 | 273.94 | 309.57 | 3.10 |
| | 275 | 409.79 | 416.47 | 409.79 | 354.11 | 345.21 | 387.08 | 6.95 |
| | 300 | 632.51 | 581.28 | 587.96 | 505.56 | 496.65 | 560.79 | 19.15 |
| | 325 | 1013.35 | 1111.34 | 1131.38 | 979.94 | 962.12 | 1039.63 | |
| Retraction 3 | 325 | 1013.35 | 1111.34 | 1131.38 | 979.94 | 962.12 | 1039.63 | 25.09 |
| | 300 | 449.88 | 438.75 | 436.52 | 371.93 | 365.25 | 412.47 | 3.74 |
| | 275 | 336.30 | 345.21 | 342.98 | 287.30 | 282.85 | 318.93 | 2.55 |
| | 250 | 269.48 | 278.39 | 273.94 | 231.62 | 222.71 | 255.23 | 2.41 |
| | 225 | 207.12 | 216.03 | 209.35 | 175.94 | 167.03 | 195.10 | 2.87 |
| | 200 | 131.40 | 144.76 | 133.63 | 111.36 | 95.77 | 123.38 | 3.40 |
| | 175 | 46.77 | 57.91 | 40.09 | 33.41 | 13.36 | 38.31 | |

TABLE 10

| Extension/Retraction | Embodiment 1 Avg. | Slope | Embodiment 2 Avg. | Slope | Sample 1 Avg. | Slope | Sample 2 Avg. | Slope | Sample 3 Avg. | Slope | Sample 4 Avg. | Slope | Sample 5 Avg. | Slope | Sample 6 Avg. | Slope | Sample 7 Avg. | Slope |
|---|---|---|---|---|---|---|---|---|---|---|---|---|---|---|---|---|---|---|
| Extension 1 | | | | | | | | | | | | | | | | | | |
| 175 | 113.03 | 2.10 | 116.14 | 2.37 | 196.69 | 2.95 | −2.67 | 3.03 | 412.42 | 7.75 | −1.78 | 5.58 | 238.52 | 2.63 | 217.11 | 4.18 | 115.37 | 3.55 |
| 200 | 165.54 | 1.78 | 175.33 | 1.96 | 270.56 | 2.67 | 72.96 | 4.66 | 606.39 | 7.55 | 137.80 | 8.05 | 304.37 | 2.55 | 321.66 | 3.67 | 204.01 | 2.90 |
| 225 | 210.04 | 1.58 | 224.26 | 1.85 | 337.30 | 2.92 | 189.53 | 3.47 | 795.03 | 9.13 | 339.16 | 6.17 | 368.01 | 3.10 | 413.31 | 3.74 | 276.61 | 2.67 |
| 250 | 249.64 | 1.42 | 270.56 | 1.67 | 410.28 | 4.08 | 276.28 | 2.67 | 1023.26 | 11.66 | 493.41 | 5.32 | 445.44 | 4.33 | 506.74 | 4.36 | 348.32 | 3.47 |
| 275 | 285.24 | 1.53 | 312.38 | 1.80 | 512.19 | 6.67 | 343.01 | 2.51 | 1314.67 | 15.70 | 626.32 | 5.39 | 553.57 | 8.37 | 615.74 | 6.48 | 435.18 | 7.93 |
| 300 | 323.51 | 1.55 | 357.33 | 1.96 | 728.90 | 44.65 | 405.75 | 2.51 | 1707.29 | 19.81 | 761.00 | 4.57 | 762.72 | 36.07 | 777.68 | 16.75 | 633.40 | 17.46 |
| 325 | 362.22 | | 406.28 | | 1845.15 | | 468.48 | | 2202.46 | | 875.24 | | 1664.49 | | 1196.33 | | 1069.91 | |
| Retraction 1 | | | | | | | | | | | | | | | | | | |
| 325 | 362.22 | 3.33 | 406.28 | 4.45 | 1845.15 | 55.37 | 468.48 | 8.01 | 2202.46 | 50.73 | 875.24 | 12.18 | 1664.49 | 48.25 | 1196.33 | 23.08 | 1069.91 | 25.60 |
| 300 | 279.01 | 1.87 | 295.03 | 2.08 | 461.01 | 4.13 | 268.27 | 3.51 | 934.28 | 13.79 | 570.75 | 6.49 | 458.34 | 4.86 | 619.30 | 5.00 | 429.54 | 4.13 |
| 275 | 232.29 | 1.41 | 242.97 | 1.55 | 357.77 | 2.49 | 180.63 | 2.54 | 589.49 | 7.67 | 408.51 | 5.57 | 336.86 | 2.35 | 494.28 | 3.59 | 326.50 | 2.58 |
| 250 | 197.13 | 1.44 | 204.25 | 1.55 | 295.47 | 2.21 | 117.01 | 2.54 | 397.74 | 5.50 | 269.37 | 5.49 | 278.12 | 1.57 | 404.41 | 3.24 | 261.91 | 2.48 |
| 225 | 161.09 | 1.39 | 165.54 | 1.64 | 240.30 | 2.37 | 53.39 | 2.24 | 260.26 | 4.63 | 132.02 | 4.98 | 238.96 | 1.57 | 323.44 | 3.47 | 200.00 | 2.80 |
| 200 | 126.38 | 2.05 | 124.60 | 2.10 | 181.11 | 2.74 | −2.67 | 0.04 | 144.59 | 4.00 | 7.56 | 0.48 | 199.80 | 1.99 | 236.68 | 4.02 | 130.05 | 3.40 |
| 175 | 75.20 | | 72.09 | | 112.58 | | −3.56 | | 44.49 | | −4.45 | | 149.96 | | 136.14 | | 44.99 | |
| Extension 2 | | | | | | | | | | | | | | | | | | |
| 175 | 86.77 | 2.14 | 87.22 | 2.26 | 149.96 | 3.03 | −4.00 | 0.75 | 154.38 | 6.10 | −4.45 | 2.08 | 185.12 | 2.63 | 171.28 | 4.25 | 74.39 | 3.85 |
| 200 | 140.17 | 1.71 | 143.73 | 1.83 | 225.61 | 2.60 | 14.68 | 3.97 | 306.98 | 5.82 | 47.56 | 7.11 | 250.98 | 2.58 | 277.62 | 3.61 | 170.60 | 2.89 |
| 225 | 182.89 | 1.35 | 189.57 | 1.58 | 290.58 | 2.74 | 113.89 | 2.88 | 452.46 | 6.92 | 225.37 | 5.97 | 315.50 | 2.88 | 367.93 | 3.65 | 242.76 | 2.87 |
| 250 | 216.71 | 1.50 | 229.17 | 1.60 | 359.11 | 3.38 | 185.97 | 2.62 | 625.52 | 9.72 | 374.72 | 5.42 | 387.59 | 3.77 | 459.13 | 4.18 | 314.47 | 3.24 |
| 275 | 254.09 | 1.57 | 269.22 | 1.92 | 443.66 | 6.87 | 251.37 | 3.31 | 868.44 | 16.19 | 510.30 | 5.87 | 481.93 | 7.01 | 563.68 | 6.05 | 395.54 | 7.50 |
| 300 | 293.25 | 1.69 | 317.28 | 1.94 | 615.42 | 47.83 | 334.12 | 4.43 | 1273.29 | 28.15 | 656.99 | 6.65 | 657.25 | 33.09 | 714.95 | 18.88 | 583.06 | 18.26 |
| 325 | 335.52 | | 365.78 | | 1811.12 | | 444.90 | | 1977.12 | | 823.23 | | 1484.49 | | 1186.98 | | 1039.53 | |
| Retraction 2 | | | | | | | | | | | | | | | | | | |
| 325 | 335.52 | 2.71 | 365.78 | 3.31 | 1811.12 | 54.45 | 444.90 | 7.44 | 1977.12 | 43.48 | 823.23 | 10.92 | 1484.49 | 41.72 | 1186.98 | 23.19 | 1039.53 | 24.85 |
| 300 | 267.89 | 1.76 | 283.02 | 1.96 | 449.89 | 3.93 | 258.93 | 3.36 | 890.24 | 12.94 | 550.30 | 6.37 | 441.43 | 4.54 | 607.28 | 4.84 | 416.26 | 3.88 |
| 275 | 223.83 | 1.30 | 234.07 | 1.44 | 351.54 | 2.47 | 174.84 | 2.60 | 566.80 | 7.45 | 391.17 | 5.44 | 327.96 | 2.22 | 486.27 | 3.49 | 321.15 | 2.55 |
| 250 | 191.35 | 1.32 | 198.02 | 1.51 | 289.69 | 2.14 | 109.89 | 2.51 | 380.39 | 5.30 | 255.15 | 5.41 | 272.34 | 1.58 | 399.07 | 3.24 | 257.46 | 2.39 |
| 225 | 158.42 | 1.46 | 160.20 | 1.57 | 236.29 | 2.33 | 47.16 | 2.05 | 247.81 | 4.64 | 120.02 | 4.69 | 232.73 | 1.60 | 316.10 | 3.47 | 197.77 | 2.90 |
| 200 | 121.93 | 1.90 | 121.04 | 2.06 | 178.00 | 2.76 | −4.00 | −0.02 | 131.69 | 3.95 | 2.67 | 0.20 | 192.68 | 1.98 | 231.35 | 4.02 | 125.16 | 3.40 |
| 175 | 74.31 | | 69.42 | | 109.02 | | −3.56 | | 32.92 | | −2.22 | | 143.29 | | 130.80 | | 40.09 | |

TABLE 10-continued

| Extension/ Retraction | Embodiment 1 Avg. | Slope | Embodiment 2 Avg. | Slope | Sample 1 Avg. | Slope | Sample 2 Avg. | Slope | Sample 3 Avg. | Slope | Sample 4 Avg. | Slope | Sample 5 Avg. | Slope | Sample 6 Avg. | Slope | Sample 7 Avg. | Slope |
|---|---|---|---|---|---|---|---|---|---|---|---|---|---|---|---|---|---|---|
| Extension 3 | | | | | | | | | | | | | | | | | | |
| 175 | 84.10 | 2.10 | 83.21 | 2.31 | 141.51 | 3.06 | -4.00 | 0.53 | 134.36 | 6.25 | -4.45 | 1.51 | 178.00 | 2.67 | 165.06 | 4.31 | 67.70 | 3.90 |
| 200 | 136.61 | 1.76 | 141.06 | 1.82 | 218.05 | 2.69 | 9.34 | 3.75 | 290.96 | 5.64 | 33.34 | 7.25 | 244.75 | 2.47 | 272.72 | 3.58 | 165.25 | 3.08 |
| 225 | 180.67 | 1.37 | 186.45 | 1.51 | 285.24 | 2.69 | 103.22 | 2.99 | 431.99 | 6.54 | 214.70 | 5.80 | 306.60 | 2.87 | 362.15 | 3.68 | 242.31 | 2.69 |
| 250 | 214.93 | 1.33 | 224.28 | 1.53 | 352.43 | 3.44 | 177.96 | 2.47 | 597.94 | 9.08 | 359.61 | 5.21 | 378.24 | 3.68 | 454.24 | 3.97 | 309.57 | 3.10 |
| 275 | 248.31 | 1.53 | 262.55 | 1.85 | 438.32 | 6.34 | 239.80 | 3.22 | 824.84 | 15.13 | 489.85 | 5.71 | 470.36 | 6.64 | 553.45 | 5.84 | 387.08 | 6.95 |
| 300 | 286.58 | 1.67 | 308.82 | 1.96 | 596.73 | 42.69 | 320.33 | 4.66 | 1203.00 | 28.09 | 632.54 | 6.70 | 636.34 | 36.65 | 699.38 | 17.19 | 560.79 | 19.15 |
| 325 | 328.40 | | 357.77 | | 1664.05 | | 436.89 | | 1905.27 | | 800.12 | | 1552.58 | | 1129.15 | | 1039.63 | |
| Retraction 3 | | | | | | | | | | | | | | | | | | |
| 325 | 328.40 | 2.56 | 357.77 | 3.10 | 1664.05 | 48.76 | 436.89 | 7.28 | 1905.27 | 41.51 | 800.12 | 10.49 | 1552.58 | 44.62 | 1129.15 | 21.05 | 1039.63 | 25.09 |
| 300 | 264.33 | 1.67 | 280.35 | 1.87 | 444.99 | 3.84 | 254.93 | 3.31 | 867.55 | 12.47 | 537.86 | 6.15 | 436.98 | 4.45 | 602.83 | 4.84 | 412.47 | 3.74 |
| 275 | 222.50 | 1.30 | 233.62 | 1.46 | 348.87 | 2.58 | 172.17 | 2.60 | 555.67 | 7.39 | 384.06 | 5.41 | 325.73 | 2.24 | 481.82 | 3.45 | 318.93 | 2.55 |
| 250 | 190.01 | 1.35 | 197.13 | 1.53 | 284.35 | 2.05 | 107.22 | 2.54 | 371.04 | 5.27 | 248.93 | 5.35 | 269.67 | 1.53 | 395.51 | 3.19 | 255.23 | 2.41 |
| 225 | 156.19 | 1.41 | 158.86 | 1.58 | 233.18 | 2.30 | 43.60 | 1.89 | 239.35 | 4.59 | 115.13 | 4.59 | 231.40 | 1.60 | 315.88 | 3.49 | 195.10 | 2.87 |
| 200 | 121.04 | 1.92 | 119.26 | 2.10 | 175.77 | 2.79 | -3.56 | -0.02 | 124.57 | 3.83 | 0.44 | 0.12 | 191.35 | 2.05 | 228.68 | 4.00 | 123.38 | 3.40 |
| 175 | 72.98 | | 66.75 | | 105.91 | | -3.11 | | 28.92 | | -2.67 | | 140.17 | | 128.57 | | 38.31 | |

TABLE 11

| Extension/Retraction Cycle | Embodiment 1 Ext. Range | Embodiment 1 Avg. Slope | Embodiment 2 Ext. Range | Embodiment 2 Avg. Slope | Sample 1 Ext. Range | Sample 1 Avg. Slope | Sample 2 Ext. Range | Sample 2 Avg. Slope | Sample 3 Ext. Range | Sample 3 Avg. Slope | Sample 4 Ext. Range | Sample 4 Avg. Slope | Sample 5 Ext. Range | Sample 5 Avg. Slope | Sample 6 Ext. Range | Sample 6 Avg. Slope | Sample 7 Ext. Range | Sample 7 Avg. Slope |
|---|---|---|---|---|---|---|---|---|---|---|---|---|---|---|---|---|---|---|
| Extension 1 | 175–325 | 1.66 | 175–325 | 1.93 | 175–325 | 10.99 | 175–325 | 3.14 | 175–325 | 11.93 | 175–325 | 5.85 | 175–325 | 9.51 | 175–325 | 6.53 | 175–325 | 6.36 |
| | 200–325 | 1.57 | 200–325 | 1.85 | 200–325 | 12.60 | 200–325 | 3.16 | 200–325 | 12.77 | 200–325 | 5.90 | 200–325 | 10.88 | 200–325 | 7.00 | 200–325 | 6.93 |
| | 225–325 | 1.52 | 225–325 | 1.82 | 225–325 | 15.08 | 225–325 | 2.79 | 225–325 | 14.07 | 225–325 | 5.36 | 225–325 | 12.96 | 225–325 | 7.83 | 225–325 | 7.93 |
| | 250–325 | 1.50 | 250–325 | 1.81 | 250–325 | 19.13 | 250–325 | 2.56 | 250–325 | 15.72 | 250–325 | 5.09 | 250–325 | 16.25 | 250–325 | 9.19 | 250–325 | 9.62 |
| | 275–325 | 1.54 | 275–325 | 1.88 | 275–325 | 26.66 | 275–325 | 2.51 | 275–325 | 17.76 | 275–325 | 4.98 | 275–325 | 22.22 | 275–325 | 11.61 | 275–325 | 12.69 |
| | 300–325 | 1.55 | 300–325 | 1.96 | 300–325 | 44.65 | 300–325 | 2.51 | 300–325 | 19.81 | 300–325 | 4.57 | 300–325 | 36.07 | 300–325 | 16.75 | 300–325 | 17.46 |
| Retraction 1 | 175–325 | 1.91 | 175–325 | 2.23 | 175–325 | 11.55 | 175–325 | 3.15 | 175–325 | 14.39 | 175–325 | 5.86 | 175–325 | 10.10 | 175–325 | 7.07 | 175–325 | 6.83 |
| | 200–325 | 1.89 | 200–325 | 2.25 | 200–325 | 13.31 | 200–325 | 3.77 | 200–325 | 16.46 | 200–325 | 6.94 | 200–325 | 11.72 | 200–325 | 7.68 | 200–325 | 7.52 |
| | 225–325 | 2.01 | 225–325 | 2.41 | 225–325 | 16.05 | 225–325 | 4.15 | 225–325 | 19.42 | 225–325 | 7.43 | 225–325 | 14.26 | 225–325 | 8.73 | 225–325 | 8.70 |
| | 250–325 | 2.20 | 250–325 | 2.69 | 250–325 | 20.66 | 250–325 | 4.69 | 250–325 | 24.06 | 250–325 | 8.08 | 250–325 | 18.48 | 250–325 | 10.56 | 250–325 | 10.77 |
| | 275–325 | 2.60 | 275–325 | 3.27 | 275–325 | 29.75 | 275–325 | 5.76 | 275–325 | 32.26 | 275–325 | 9.33 | 275–325 | 26.55 | 275–325 | 14.04 | 275–325 | 14.87 |
| | 300–325 | 3.33 | 300–325 | 4.45 | 300–325 | 55.37 | 300–325 | 8.01 | 300–325 | 50.73 | 300–325 | 12.18 | 300–325 | 48.25 | 300–325 | 23.08 | 300–325 | 25.60 |
| Extension 2 | 175–325 | 1.66 | 175–325 | 1.86 | 175–325 | 11.07 | 175–325 | 2.99 | 175–325 | 12.15 | 175–325 | 5.52 | 175–325 | 8.66 | 175–325 | 6.77 | 175–325 | 6.43 |
| | 200–325 | 1.56 | 200–325 | 1.78 | 200–325 | 12.68 | 200–325 | 3.44 | 200–325 | 13.36 | 200–325 | 6.21 | 200–325 | 9.87 | 200–325 | 7.27 | 200–325 | 6.95 |
| | 225–325 | 1.53 | 225–325 | 1.76 | 225–325 | 15.21 | 225–325 | 3.31 | 225–325 | 15.25 | 225–325 | 5.98 | 225–325 | 11.69 | 225–325 | 8.19 | 225–325 | 7.97 |
| | 250–325 | 1.58 | 250–325 | 1.82 | 250–325 | 19.36 | 250–325 | 3.45 | 250–325 | 18.02 | 250–325 | 5.98 | 250–325 | 14.63 | 250–325 | 9.70 | 250–325 | 9.67 |
| | 275–325 | 1.63 | 275–325 | 1.93 | 275–325 | 27.35 | 275–325 | 3.87 | 275–325 | 22.17 | 275–325 | 6.26 | 275–325 | 20.05 | 275–325 | 12.47 | 275–325 | 12.88 |
| | 300–325 | 1.69 | 300–325 | 1.94 | 300–325 | 47.83 | 300–325 | 4.43 | 300–325 | 28.15 | 300–325 | 6.65 | 300–325 | 33.09 | 300–325 | 18.88 | 300–325 | 18.26 |
| Retraction 2 | 175–325 | 1.74 | 175–325 | 1.98 | 175–325 | 11.35 | 175–325 | 2.99 | 175–325 | 12.96 | 175–325 | 5.50 | 175–325 | 8.94 | 175–325 | 7.04 | 175–325 | 6.66 |
| | 200–325 | 1.71 | 200–325 | 1.96 | 200–325 | 13.06 | 200–325 | 3.59 | 200–325 | 14.76 | 200–325 | 6.56 | 200–325 | 10.33 | 200–325 | 7.65 | 200–325 | 7.32 |
| | 225–325 | 1.77 | 225–325 | 2.06 | 225–325 | 15.75 | 225–325 | 3.98 | 225–325 | 17.29 | 225–325 | 7.03 | 225–325 | 12.52 | 225–325 | 8.69 | 225–325 | 8.42 |
| | 250–325 | 1.92 | 250–325 | 2.24 | 250–325 | 20.29 | 250–325 | 4.47 | 250–325 | 21.29 | 250–325 | 7.57 | 250–325 | 16.16 | 250–325 | 10.51 | 250–325 | 10.43 |
| | 275–325 | 2.23 | 275–325 | 2.63 | 275–325 | 29.19 | 275–325 | 5.40 | 275–325 | 28.21 | 275–325 | 8.64 | 275–325 | 23.13 | 275–325 | 14.01 | 275–325 | 14.37 |
| | 300–325 | 2.71 | 300–325 | 3.31 | 300–325 | 54.45 | 300–325 | 7.44 | 300–325 | 43.48 | 300–325 | 10.92 | 300–325 | 41.72 | 300–325 | 23.19 | 300–325 | 24.85 |
| Extension 3 | 175–325 | 1.63 | 175–325 | 1.83 | 175–325 | 10.15 | 175–325 | 2.94 | 175–325 | 11.81 | 175–325 | 5.36 | 175–325 | 9.16 | 175–325 | 6.43 | 175–325 | 6.48 |
| | 200–325 | 1.53 | 200–325 | 1.73 | 200–325 | 11.57 | 200–325 | 3.42 | 200–325 | 12.91 | 200–325 | 6.13 | 200–325 | 10.46 | 200–325 | 6.85 | 200–325 | 6.99 |
| | 225–325 | 1.48 | 225–325 | 1.71 | 225–325 | 13.79 | 225–325 | 3.34 | 225–325 | 14.73 | 225–325 | 5.85 | 225–325 | 12.46 | 225–325 | 7.67 | 225–325 | 7.97 |
| | 250–325 | 1.51 | 250–325 | 1.78 | 250–325 | 17.49 | 250–325 | 3.45 | 250–325 | 17.43 | 250–325 | 5.87 | 250–325 | 15.66 | 250–325 | 9.00 | 250–325 | 9.73 |
| | 275–325 | 1.60 | 275–325 | 1.90 | 275–325 | 24.51 | 275–325 | 3.94 | 275–325 | 21.61 | 275–325 | 6.21 | 275–325 | 21.64 | 275–325 | 11.51 | 275–325 | 13.05 |
| | 300–325 | 1.67 | 300–325 | 1.96 | 300–325 | 42.69 | 300–325 | 4.66 | 300–325 | 28.09 | 300–325 | 6.70 | 300–325 | 36.65 | 300–325 | 17.19 | 300–325 | 19.15 |
| Retraction 3 | 175–325 | 1.70 | 175–325 | 1.94 | 175–325 | 10.39 | 175–325 | 2.93 | 175–325 | 12.51 | 175–325 | 5.35 | 175–325 | 9.42 | 175–325 | 6.67 | 175–325 | 6.68 |
| | 200–325 | 1.66 | 200–325 | 1.91 | 200–325 | 11.91 | 200–325 | 3.52 | 200–325 | 14.25 | 200–325 | 6.40 | 200–325 | 10.89 | 200–325 | 7.20 | 200–325 | 7.33 |
| | 225–325 | 1.72 | 225–325 | 1.99 | 225–325 | 14.31 | 225–325 | 3.93 | 225–325 | 16.66 | 225–325 | 6.85 | 225–325 | 13.21 | 225–325 | 8.13 | 225–325 | 8.45 |
| | 250–325 | 1.85 | 250–325 | 2.14 | 250–325 | 18.40 | 250–325 | 4.40 | 250–325 | 20.46 | 250–325 | 7.35 | 250–325 | 17.11 | 250–325 | 9.78 | 250–325 | 10.46 |
| | 275–325 | 2.12 | 275–325 | 2.48 | 275–325 | 26.30 | 275–325 | 5.29 | 275–325 | 26.99 | 275–325 | 8.32 | 275–325 | 24.54 | 275–325 | 12.95 | 275–325 | 14.41 |
| | 300–325 | 2.56 | 300–325 | 3.10 | 300–325 | 48.76 | 300–325 | 7.28 | 300–325 | 41.51 | 300–325 | 10.49 | 300–325 | 44.62 | 300–325 | 21.05 | 300–325 | 25.09 |

TABLE 12

| Extension/Retraction Cycle | Embodiment 1 Ext. Range | Embodiment 1 Avg. Slope | Embodiment 2 Ext. Range | Embodiment 2 Avg. Slope | Sample 1 Ext. Range | Sample 1 Avg. Slope | Sample 2 Ext. Range | Sample 2 Avg. Slope | Sample 3 Ext. Range | Sample 3 Avg. Slope | Sample 4 Ext. Range | Sample 4 Avg. Slope | Sample 5 Ext. Range | Sample 5 Avg. Slope | Sample 6 Ext. Range | Sample 6 Avg. Slope | Sample 7 Ext. Range | Sample 7 Avg. Slope |
|---|---|---|---|---|---|---|---|---|---|---|---|---|---|---|---|---|---|---|
| Average | 175–325 | 1.72 | 175–325 | 1.96 | 175–325 | 10.92 | 175–325 | 3.02 | 175–325 | 12.62 | 175–325 | 5.57 | 175–325 | 9.30 | 175–325 | 6.75 | 175–325 | 6.57 |
| Over | 200–325 | 1.65 | 200–325 | 1.91 | 200–325 | 12.52 | 200–325 | 3.49 | 200–325 | 14.09 | 200–325 | 6.36 | 200–325 | 10.69 | 200–325 | 7.27 | 200–325 | 7.17 |
| First | 225–325 | 1.67 | 225–325 | 1.96 | 225–325 | 15.03 | 225–325 | 3.58 | 225–325 | 16.24 | 225–325 | 6.42 | 225–325 | 12.85 | 225–325 | 8.21 | 225–325 | 8.24 |
| Three | 250–325 | 1.76 | 250–325 | 2.08 | 250–325 | 19.22 | 250–325 | 3.84 | 250–325 | 19.50 | 250–325 | 6.66 | 250–325 | 16.38 | 250–325 | 9.79 | 250–325 | 10.11 |
| Cycles | 275–325 | 1.95 | 275–325 | 2.35 | 275–325 | 27.29 | 275–325 | 4.46 | 275–325 | 24.83 | 275–325 | 7.29 | 275–325 | 23.02 | 275–325 | 12.77 | 275–325 | 13.71 |
|  | 300–325 | 2.25 | 300–325 | 2.79 | 300–325 | 48.96 | 300–325 | 5.72 | 300–325 | 35.29 | 300–325 | 8.58 | 300–325 | 40.07 | 300–325 | 20.02 | 300–325 | 21.74 |
| Average | 175–325 | 1.65 | 175–325 | 1.87 | 175–325 | 10.74 | 175–325 | 3.02 | 175–325 | 11.96 | 175–325 | 5.58 | 175–325 | 9.11 | 175–325 | 6.58 | 175–325 | 6.43 |
| Over | 200–325 | 1.56 | 200–325 | 1.79 | 200–325 | 12.28 | 200–325 | 3.34 | 200–325 | 13.01 | 200–325 | 6.08 | 200–325 | 10.40 | 200–325 | 7.04 | 200–325 | 6.96 |
| First | 225–325 | 1.51 | 225–325 | 1.77 | 225–325 | 14.69 | 225–325 | 3.15 | 225–325 | 14.68 | 225–325 | 5.73 | 225–325 | 12.37 | 225–325 | 7.90 | 225–325 | 7.96 |
| Three | 250–325 | 1.53 | 250–325 | 1.80 | 250–325 | 18.66 | 250–325 | 3.16 | 250–325 | 17.06 | 250–325 | 5.65 | 250–325 | 15.51 | 250–325 | 9.30 | 250–325 | 9.67 |
| Extensions | 275–325 | 1.59 | 275–325 | 1.90 | 275–325 | 26.17 | 275–325 | 3.44 | 275–325 | 20.51 | 275–325 | 5.81 | 275–325 | 21.30 | 275–325 | 11.86 | 275–325 | 12.88 |
|  | 300–325 | 1.64 | 300–325 | 1.95 | 300–325 | 45.06 | 300–325 | 3.87 | 300–325 | 25.35 | 300–325 | 5.97 | 300–325 | 35.27 | 300–325 | 17.61 | 300–325 | 18.29 |
| Average | 175–325 | 1.79 | 175–325 | 2.05 | 175–325 | 11.10 | 175–325 | 3.02 | 175–325 | 13.29 | 175–325 | 5.57 | 175–325 | 9.48 | 175–325 | 6.93 | 175–325 | 6.72 |
| Over | 200–325 | 1.75 | 200–325 | 2.04 | 200–325 | 12.76 | 200–325 | 3.63 | 200–325 | 15.16 | 200–325 | 6.63 | 200–325 | 10.98 | 200–325 | 7.51 | 200–325 | 7.39 |
| First | 225–325 | 1.83 | 225–325 | 2.15 | 225–325 | 15.37 | 225–325 | 4.02 | 225–325 | 17.79 | 225–325 | 7.10 | 225–325 | 13.33 | 225–325 | 8.52 | 225–325 | 8.52 |
| Three | 250–325 | 1.99 | 250–325 | 2.36 | 250–325 | 19.78 | 250–325 | 4.52 | 250–325 | 21.94 | 250–325 | 7.67 | 250–325 | 17.25 | 250–325 | 10.28 | 250–325 | 10.55 |
| Retractions | 275–325 | 2.32 | 275–325 | 2.79 | 275–325 | 28.41 | 275–325 | 5.48 | 275–325 | 29.15 | 275–325 | 8.77 | 275–325 | 24.74 | 275–325 | 13.67 | 275–325 | 14.55 |
|  | 300–325 | 2.87 | 300–325 | 3.62 | 300–325 | 52.86 | 300–325 | 7.58 | 300–325 | 45.24 | 300–325 | 11.20 | 300–325 | 44.86 | 300–325 | 22.44 | 300–325 | 25.18 |

TABLE 13

DECAY (grams)

| Extension (mm) | Embodiment 1 | Embodiment 2 | Sample 1 | Sample 2 | Sample 3 | Sample 4 | Sample 5 | Sample 6 | Sample 7 |
| --- | --- | --- | --- | --- | --- | --- | --- | --- | --- |
| 175 | 40.05 | 49.39 | 90.78 | 0.44 | 383.50 | 0.89 | 98.34 | 88.53 | 77.06 |
| 200 | 44.50 | 56.07 | 94.78 | 76.52 | 481.82 | 137.35 | 113.03 | 92.98 | 80.62 |
| 225 | 53.84 | 65.41 | 104.13 | 145.93 | 555.67 | 224.03 | 136.61 | 97.43 | 81.51 |
| 250 | 59.63 | 73.42 | 125.93 | 169.06 | 652.22 | 244.48 | 175.77 | 111.22 | 93.09 |
| 275 | 62.74 | 78.76 | 163.31 | 170.84 | 758.99 | 242.26 | 227.84 | 133.91 | 116.26 |
| 300 | 59.18 | 76.98 | 283.91 | 150.82 | 839.74 | 223.14 | 325.73 | 174.84 | 220.93 |
| Average | 53.32 | 66.67 | 143.81 | 118.94 | 611.99 | 178.69 | 179.55 | 116.49 | 111.58 |

Table 1 represents Embodiment 1 described above, and which generally corresponds to elongate elastic member 66 (FIG. 2) being joined to elongate sleeve member 62 at locations corresponding to seams 34 (FIG. 1). Table 2 represents Embodiment 2, which is similar to Embodiment 1, except that in Embodiment 2 the elastic member is selectively intermittently joined to the elongate sleeve member. The intermittent pattern of joining is a pattern of 1.27 centimeter (0.5 inch) wide adhesive zones separated by 1.27 centimeter wide zones with no adhesive. Table 3 represents Sample 1, Table 4 represents Sample 2, Table 5 represents Sample 3, Table 6 represents Sample 4, Table 7 represents Sample 5, Table 8 represents Sample 6, and Table 9 represents Sample 7.

The below-described test procedure was applied to five specimen elastic waistbands of five products of each of the Embodiments 1-2 Samples 1-7 to generate the data in Tables 1-13. After describing the test procedure, one example of a calculation will be provided.

Test Procedure

This test procedure is entitled "SINTECH TESTWORKS® Cycle Testing Program for Elastomeric Waistbands." The test procedure involves the following equipment:

(1) Sintech and TestWorks® version 2.11 software with a tensile tester with an equivalent computerized data-acquisition system, and a 25 pound load cell. Although this test procedure is designed for the Sintech TestWorks® system, it can be performed with other test systems that can be programmed to calculate the required parameters.

(2) User's Guide for Sintech TestWorks™ Program, (3) Peg/pin fixtures that are clamped into each of the two pneumatic grips/jaws of the Sintech Tester, with one of the fixtures on the movable block at the top, and the other fixture on the stationary block at the bottom.

Specimen preparation requires that used product, or product that has been tested for other purposes, not be used. A finished product is required, in which "finished product" refers to a product manufactured to be used for its intended purpose, such as a product removed from a bag purchased from any suitable facility, such as a grocery store. With the finished product in the retracted state, the elastic waistband is cut off from the top of the waist opening so that the cut-off portion includes the full width of the elastic member or element, and ensuring that the full length of the waistband maintains its closed-loop form, i.e., ensuring the waistband is not cut through its circumferential length. It was sufficient for the elastic waistbands to be cut 2.38 centimeters (15/16 inch) in width at the waist opening, ensuring that the elastic waistband included the full width of the elastic member or element.

The test parameters for the procedure are as follows:

(1) a crosshead speed of 500 millimeters per minute, (2) a gage length of 150 millimeters, and (3) waist tension values, in grams, taken at designated 25 millimeter increments in the extension range of 150 millimeters to 325 millimeters.

The procedure for preparing the test equipment is as follows:

(1) Verify the 25 pound load cell is in the Sintech Tester. The load cell must warm up a minimum of 30 minutes.

(2) Boot up the Sintech, and if necessary, type in the operator identification and press Enter. Use the arrow keys or mouse to highlight the heading desired.

(3) Highlight "Test" on the main menu, and press Enter.

(4) Highlight "Method" on the Test Menu, and press Enter.

(5) Highlight "CSD Standard", and press Enter.

(6) Highlight "Cycle Test 150-325 mm", and press Enter.

(7) Highlight "Test" from the Test Menu, and press Enter.

(8) Enter the Sample identification code, and press Enter.

(9) Clamp into each of the two pneumatic grips/jaws of the Sintech Tester the pin/peg fixtures, with one on the movable block at the top, and the other on the stationary block at the bottom. Ensure that the upper and lower pin/peg fixtures are vertically aligned. Press "T" to tare load and weight of fixtures.

(10) Press F9. Adjust the fixture distance to 150 millimeters from the top end of the top fixture to the bottom end of the lower fixture. To accomplish this, press "G" for crosshead movement and indicate the number of millimeters needed to obtain the 150 millimeter gage length. Press "Z" for zero extension. Press Escape for the Test Menu.

(11) Highlight "Calibrate" for calibration, and press Enter. Follow the TestWorks® menu program for calibration of the load cell, with reference to the User Guide for more information on Load Cell Calibration if necessary. The load cell must be calibrated whenever the load cell is changed, and at the beginning of each day/shift.

(12) Press Escape when calibration is completed to return to the Test Menu.

The testing steps are as follows:

(1) Place the closed-loop elastic waistband area onto the grooved section of the top pin/peg fixture at the seamed portion of the elastic waistband, and press F9.

(2) Press "T" to tare the load.

(3) Press Escape to return to the Test Menu.

(4) Place the other end of the waistband on the bottom pin/peg fixture, with one seam on the top fixture and the other seam on the bottom fixture.

(5) Highlight "Run", and press Enter. The test will start and stop automatically, and will return to the 150 millimeter gage length at completion.

(6) When the run is completed, highlight either "File" if data and graphs are to be saved, or "Next" to save only the data. Using either "File" or "Next" will bring up the "Test" screen for the next specimen. Remove the waistband from the tester.

(7) Repeat steps 1–6 for the five specimens until the testing is complete.

(8) Refer to the User's Guide for Sintech TestWorks protocol to export data into an appropriate spreadsheet software package.

This test procedure was performed on Embodiments 1 and 2 and Samples 1–7. By way of example with reference to Table 9, five elastic waistband specimens from five products of Sample 7 (Oyasumi Man product) were individually run through the first three cycles. The tension in grams at millimeter increments between 175–325 millimeters is presented in the first five columns of Table 9 under the heading "TENSION (gms)". At each 25 mm increment for the five specimens, the five tensions in grams were averaged and appear in the "Average" column. Then, for example, by subtracting the average tension of 204.01 grams at 200 millimeters of Extension 1 from the average tension of 115.37 grams at 175 millimeters of Extension 1, and dividing that difference by the 25 millimeter increment, there results an average slope of 3.55 grams per millimeter between 175 millimeters to 200 millimeters in Extension 1; this 3.55 slope value appears in the "Slope (g/mm)" column. Similar average slopes were calculated for all of the 25 millimeter increments in the first three cycles.

Table 10 presents the data from the "Average" and "Slope" columns of Tables 1–9 for Embodiments 1 and 2, and Samples 1–7.

Table 11 presents the average slopes (g/mm) at selected extension ranges and retraction ranges for the extensions and retractions of the first three cycles. For example, Sample 7 has an average slope of 6.36 g/mm in the extension range of 175–325 millimeters for the extension of the first cycle; the first cycle including Extension 1 and Retraction 1. Similarly, for the retraction of the first cycle in the 175–325 millimeter range, Sample 7 has an average slope of 6.83 g/mm. These values are calculated from the data in Table 10. For example, in Table 11, the average slope of 6.36 g/mm for Sample 7 in the extension range of 175–325 millimeters of the first cycle is calculated by averaging, from Table 10, the six slope values for Sample 7 between 175 millimeters and 325 millimeters for Extension 1.

From the data in Table 11, there is calculated for Embodiments 1–2 and Samples 1–7, an overall average slope for (1) the first three cycles, (2) the three extensions of the first three cycles, and (3) the three retractions of the first three cycles within specific ranges. These overall average slopes are presented in Table 12. For example, Embodiment 1 has an overall average slope over the first three cycles of about 1.96 grams per millimeter in the range of 175–325 millimeters. The slope of 1.96 g/mm is calculated by averaging the slope of 1.98 g/mm over the first three extensions and the slope of 2.05 g/mm over the first three retractions. As can be clearly seen in Table 12, Embodiments 1–2 have much lower overall average slopes for the first three cycles, the first three extensions, and the first three retractions, than Samples 1–7. These overall average slopes in Table 12 are termed average maximum rates of change of modulus of the elasticity over the first three cycles within the identified range.

By providing lower average maximum rates of change of modulus of elasticity over the first three cycles, there is provided a substantially uniform low tension over a wide size range, a more comfortable fit, and improved ease of use.

Training pant 20 can be made of any suitable materials well known in the field of personal care absorbent articles. For example, absorbent structure 38 can comprise any suitable absorbent material, natural or synthetic, or a combination thereof, along with superabsorbent material. The absorbent material of which absorbent structure is made may also be encased in a tissue wrap (not shown) in order to maintain the integrity of the absorbent material. Suitable superabsorbent materials are available from various vendors, such as Stockhausen, Inc., Dow Chemical Company, Hoechst-Celanese Corporation, and Allied Colloids, Inc. Typically, the superabsorbent material is capable of absorbing at least about 15 times its weight in water, and desirably is capable of absorbing more than about 25 times its weight in water. A suitable natural absorbent material is a wood pulp fluff identified by the trade designation CR 1654 from Kimberly-Clark Corporation, Neenah, Wis. This particular wood pulp fluff is a bleached, highly absorbent sulfate wood pulp fluff containing soft wood fibers.

Outer cover layer 46 may be a single layer of a liquid permeable or liquid impermeable material, and may or may not have breathability, i.e., be vapor permeable. In this particular embodiment, outer cover layer 46 is a two-layer composite comprising outer layer 50 and inner layer 52. Outer layer 50 is a liquid permeable, nonwoven bicomponent web having a basis weight between about 15 to about 35 gsm. The nonwoven bicomponent web may be a spunbond bicomponent web, or a bonded carded bicomponent web. Suitable bicomponent fibers are a wettable, polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, or end-to-end. An alternative suitable material is a liquid permeable spunbond polypropylene nonwoven web having a basis weight between about 15 gsm to about 50 gsm.

Inner layer 52 is desirably a 0.0015 centimeter polyethylene film from Edison Plastics Company, Newport News, Va.

Liner 48 is a liquid permeable, substantially hydrophobic material, such as a spunbonded web, meltblown web, bonded carded web of synthetic polymer filaments, or combined synthetic filaments with natural fibers, such as rayon. Suitable synthetic polymers include, by way of example, polyethylene, polypropylene, and polyester. Liner 48 typically has a pore size that readily allows the passage of liquids, such as urine and other body exudates. If desired, liner 48 can be treated with a surfactant to selectively adjust its degree of wettability, and can also be selectively embossed or perforated with discrete slits or holes. Liner 48 desirably has a basis weight between about 10 gsm to about 30 gsm.

All of the described adhesives, such as adhesives 54, 56, 72, 74, can be any adhesives suitable for joining the identified materials. Suitable adhesives can be obtained from Findley Adhesives, Inc., Wauwatosa, Wis., or obtained from National Starch and Chemical Co., Bridgewater, N.J. The adhesives can be applied in any manner, such as by spraying, slot-coat extrusion, printing, or the like. The applied adhesive can be in any desired configuration, such as continuous or discontinuous beads, continuous or discontinuous swirls, meltblown patterns, spray patterns, or the like.

Elongate sleeve member 62 of waist elastic system 60 can be a nonwoven bicomponent web comprising about 50 percent polypropylene fibers and 50 percent polyethylene fibers in a side-by-side orientation, and having a basis weight of about 17 gsm. This particular type of material can be purchased from BASF Corporation, Charlotte, N.C. Other materials suitable for use in elongate sleeve member 62 include a 13 gsm spunbond polypropylene web, or a 13 gsm spunbond polyester web. Elastic member 66 is desirably made of natural rubber, or an elastomeric material such as isoprene purchasable from JPS Elastomerics Company, Holyoke, Me. Elastic member 66, as earlier described above, can be a single ribbon of material, or a plurality of strands or ribbons of elastic material. A desired material for use as a plurality of strands of elastic are LYCRA® 940 decitex, which can be purchased from E.I. DuPont de Nemours Company, Wilmington, Del.

Another important factor in providing a substantially uniform low tension over a wide size range, a more comfortable fit, and improved ease of use, is the maximum magnitude of decay, measured in grams of tension, at a specific extension over the first three cycles. For ease of explanation and understanding, and by way of example, the following description is made with reference to FIG. 9. The first three cycles of Embodiment 1 are identified as cycle 1, cycle 2, and cycle 3. Decay over the first three cycles 1, 2, and 3 is calculated by selecting an extension, for example 300 millimeters, and identifying the extension curve E1 for cycle 1 and the retraction curve R3 for cycle 3, and then subtracting the tension in grams at E1 from the tension in grams at R3. This difference represents the decay, ie. the loss of tension in grams, over the first three cycles at an extension of 300 millimeters.

Figure 9:
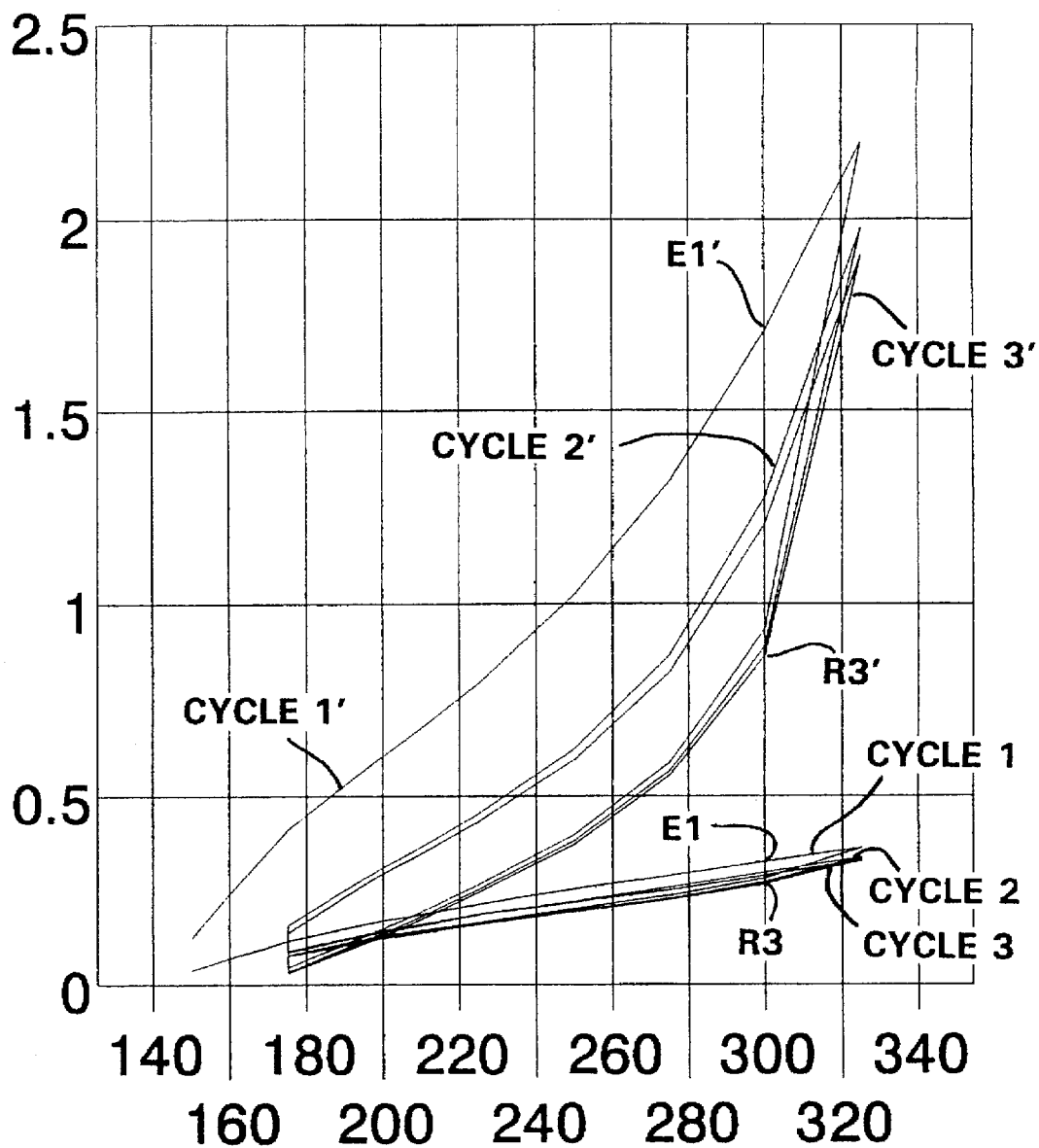
Figure 10:
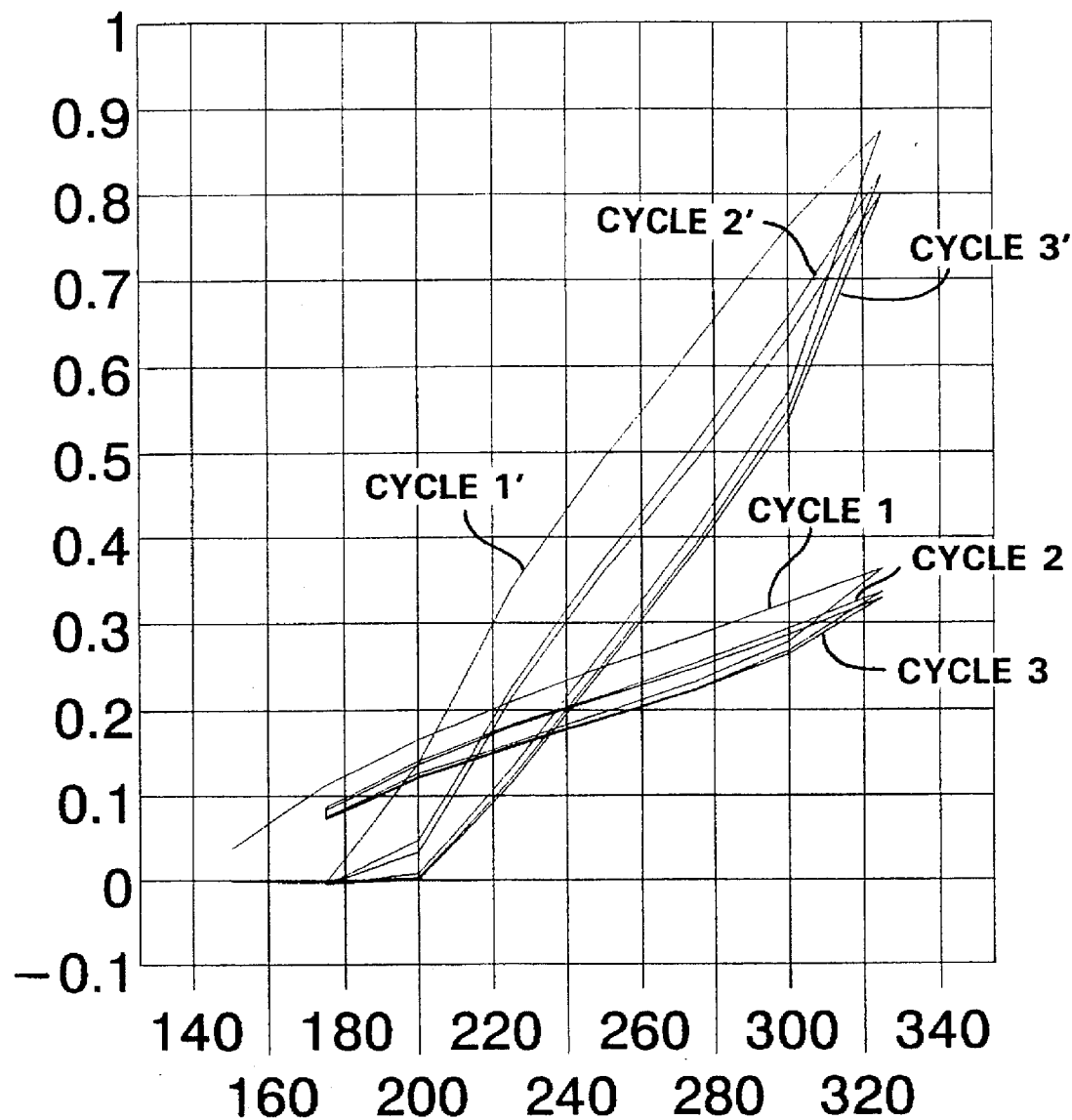
Figure 11:
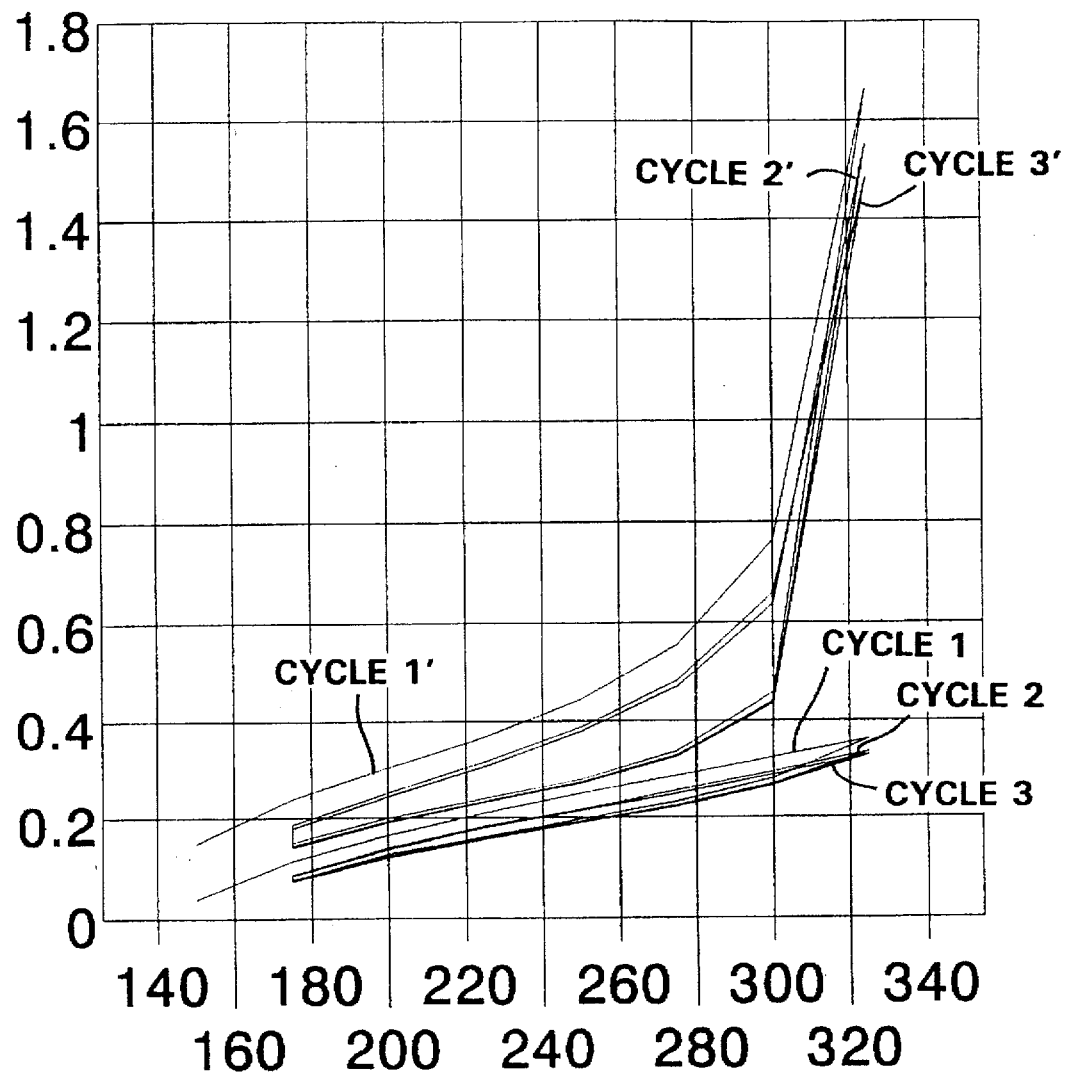
Figure 12:
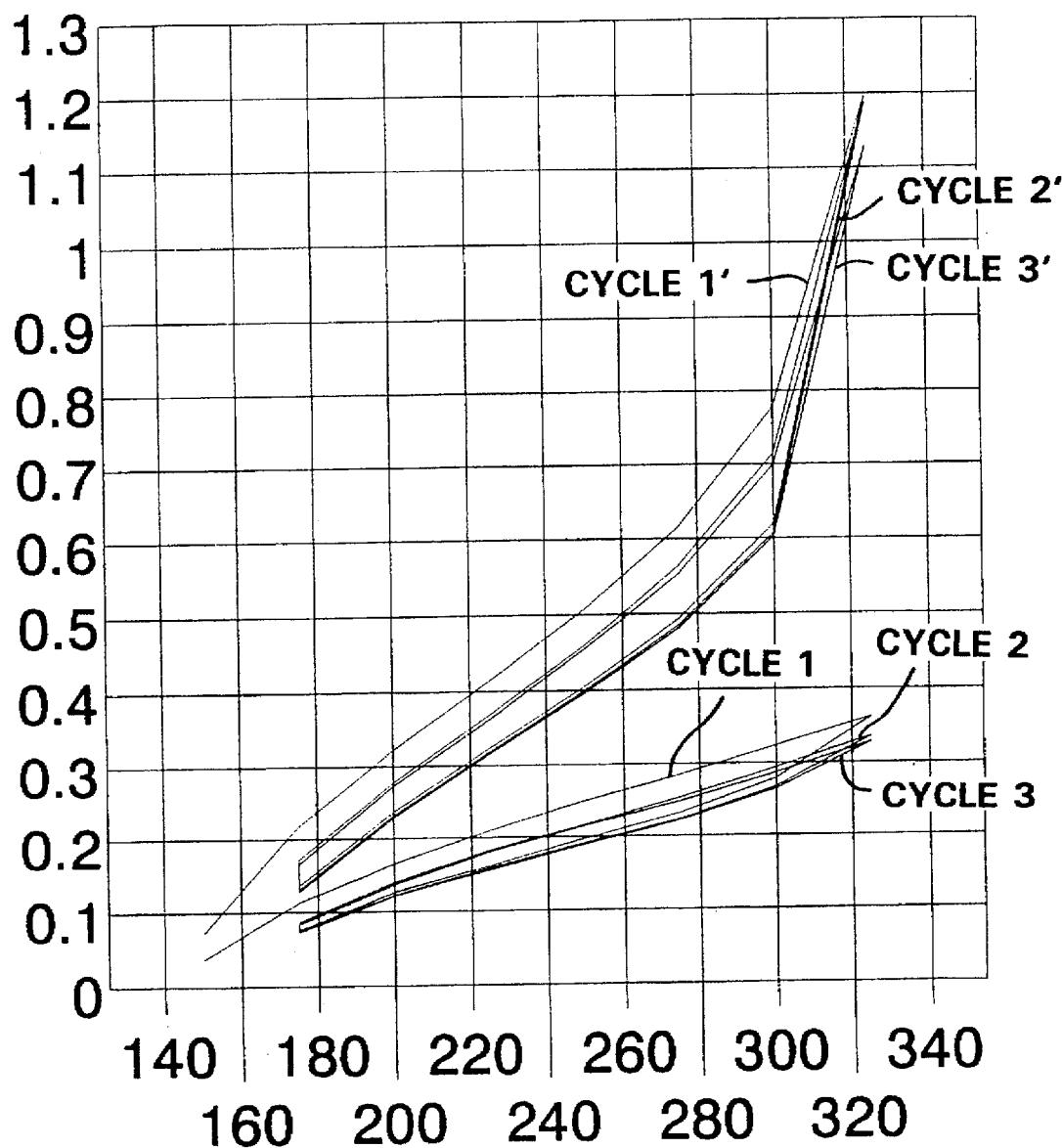
Figure 13:
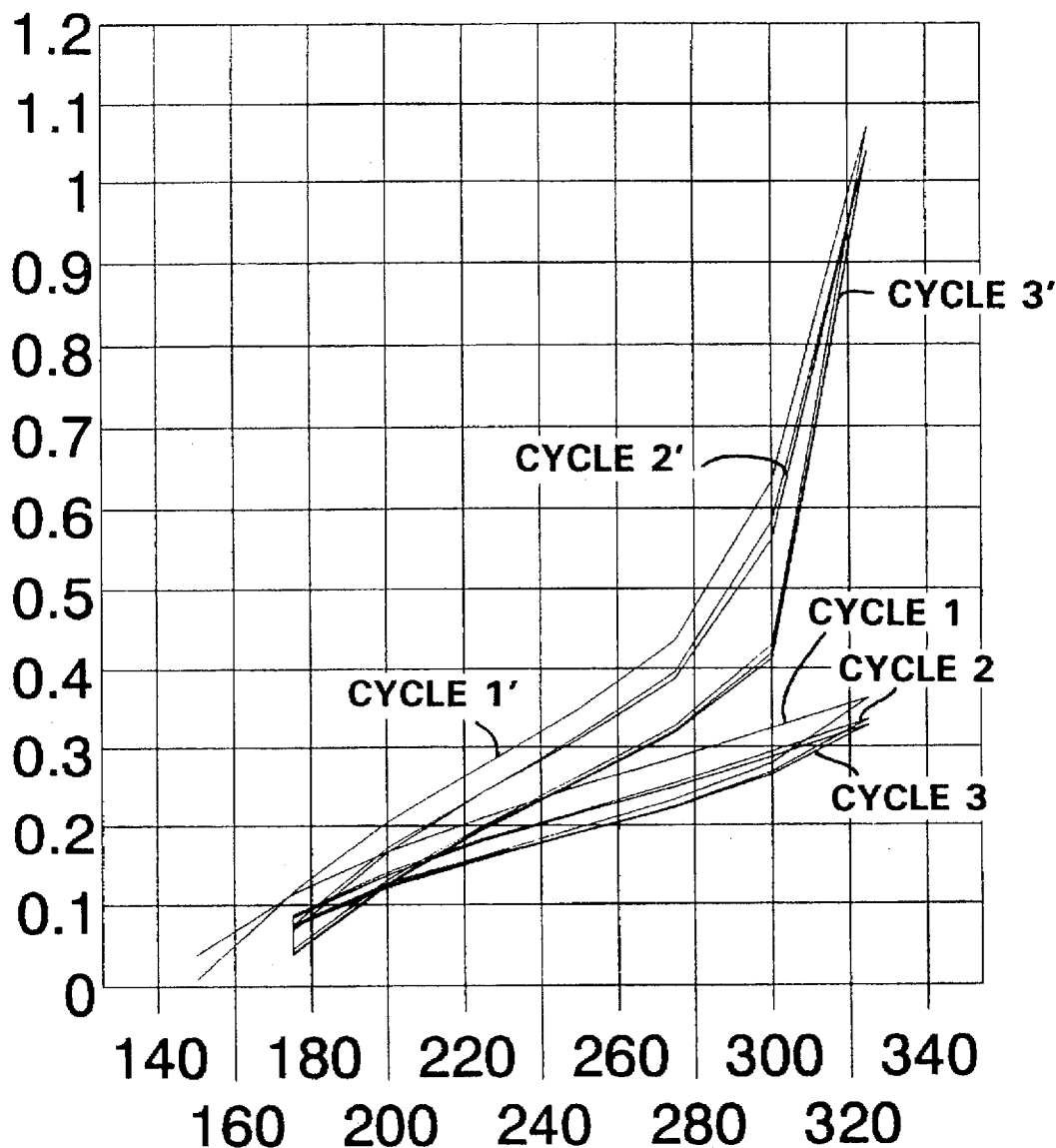

Similarly, and continuing with reference to FIG. 9, Sample 3 is represented by cycle 1', cycle 2', and cycle 3'. The decay over the first three cycles for Sample 3, measured at an extension of 300 millimeters, is the difference in grams at extension E1' of cycle 1' and the retraction R3' of cycle 3'. FIG. 9 clearly illustrates that the decay over the first three cycles of Embodiment 1 is significantly less than the decay over the first three cycles of Sample 3.

With reference to Table 13, the decay of Embodiments 1–2 and Samples 1–7 are tabulated at 25 millimeter increments in the range of 175 millimeters to 300 millimeters. At an extension of 300 millimeters, for example, Embodiment 1 results in a decay of 59.18 grams over the first three cycles, and Embodiment 2 results in a decay of 76.98 grams over the first three cycles. These decay values are significantly lower than the decay values at 300 millimeters for Samples 1–7. For example, at an extension of 300 millimeters, Sample 2 has a decay over the first three cycles of 150.82 grams, and Sample 3 has a decay over the first three cycles of 839.74 grams.

Figure 5:
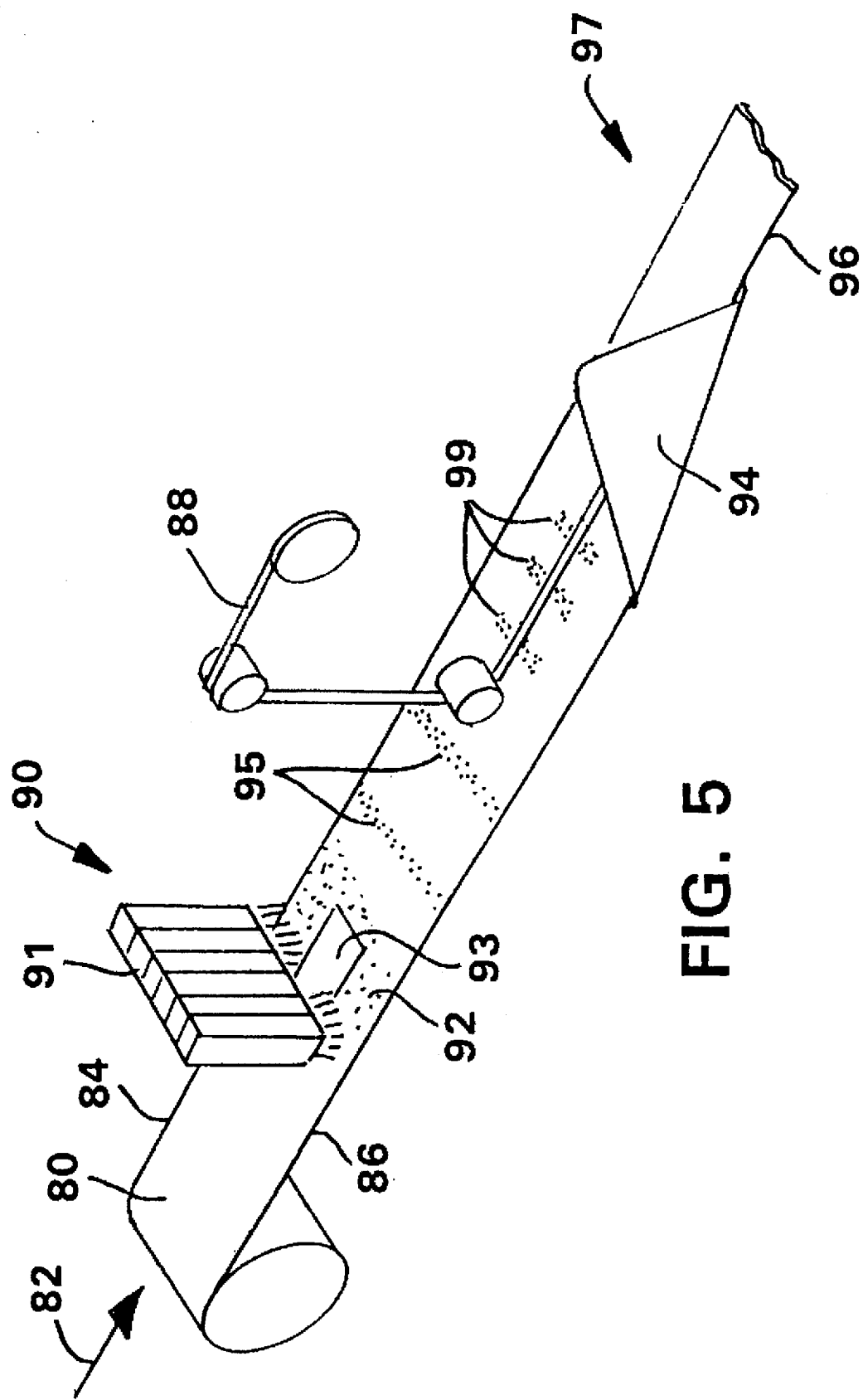
FIGS. 5 and 6 schematically illustrate one process for making a training pant similar to that represented in FIG. 2.
Figure 6:
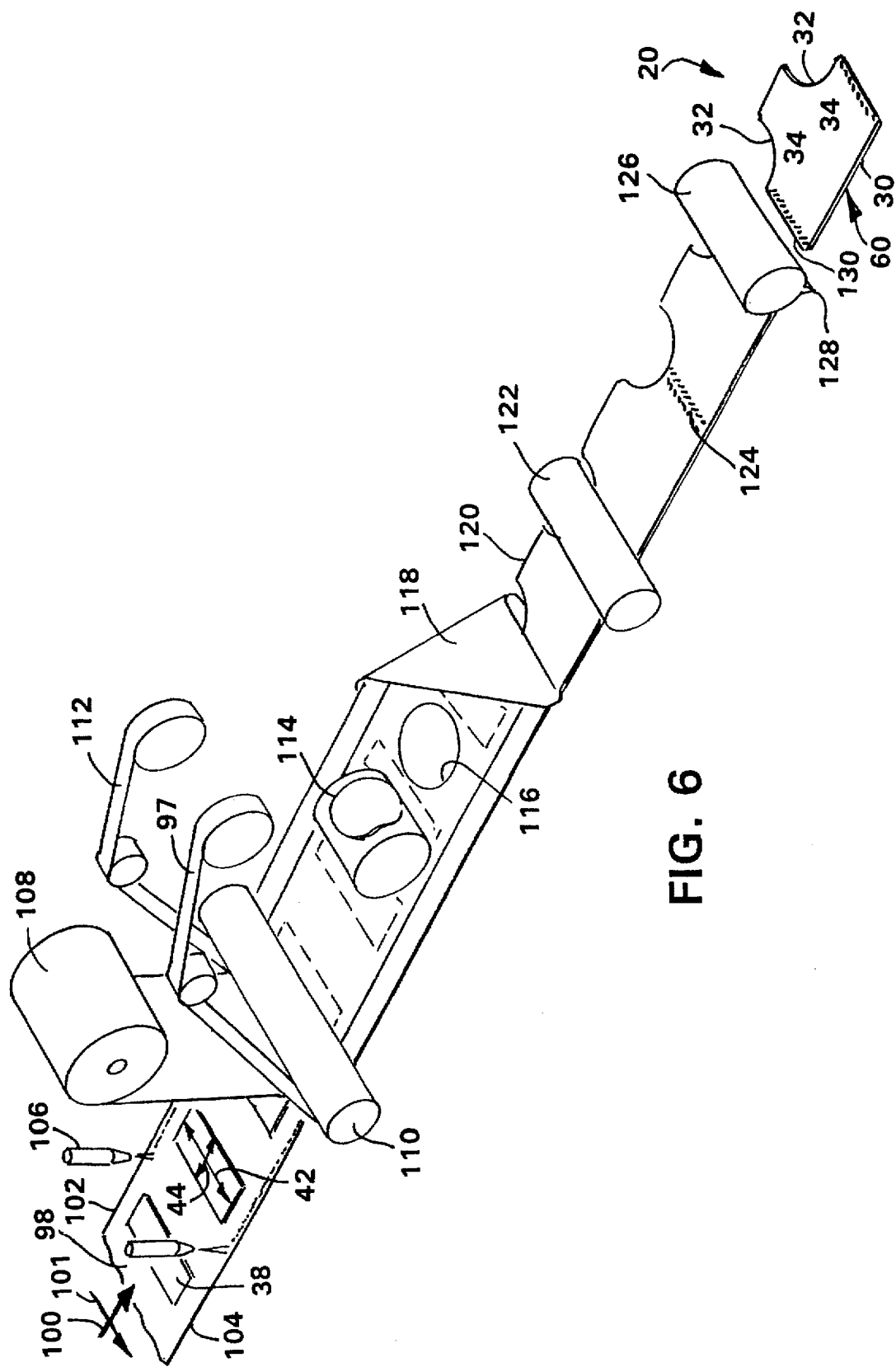

Referring now primarily to FIGS. 5 and 6, one process will be described of a manufacturing assembly line for making a disposable absorbent training pant 20. In FIG. 5, a first layer 80 of a material having opposite edge portions 84, 86 is continuously moved in a first direction 82. The first layer 80 can be supplied in any suitable manner well known in the art, and subsequently will form part of elongate sleeve member 62 (FIG. 2). An elongate elastic member 88 is continuously applied or provided in first direction 82, in any suitable manner well known in the art, in a selectively tensioned state to first layer 80. Elongate elastic member 88 will subsequently form part of elongate elastic member 66 (FIG. 2). Elongate elastic member 88 can also be continuously applied or provided in a substantially untensioned manner, and, if so, it may be a specific type of elastomeric material commonly referred to as a heat-elasticizable material. This latter type of elastomeric material can be treated, such as by heat, to recover its latent elasticity. Generally, elongate elastic member 88 will be joined to first layer 80, prior to the folding of first layer 80, by a pulsed adhesive system 90 for providing a predetermined adhesive pattern on first layer 80 by selectively controlling a bank of spray nozzles 91. The adhesive may be sprayed or applied in a continuous pattern or an intermittent pattern. One system suitable for use is the pulsed adhesive system described in European Patent Application 0 603 748 A1, the contents of which are incorporated by reference herein. The adhesive can also be supplied in other suitable manners, such as by extrusion slot coating or by a patterned adhesive roll (not shown).

The pulsed adhesive system 90 can apply adhesive in any desired pattern. For example, pulsed adhesive system 90 can apply an adhesive pattern, such as adhesive zone 92 (FIG. 5) having a window 93 that is void of adhesive. Another adhesive pattern that can be applied by pulsed adhesive system 90 is represented by adhesive zones 95 which extend substantially across first layer 80 in a direction transverse to first direction 82. Yet another adhesive pattern is illustrated by adhesive zones 99 which are applied intermittently and more closely spaced together than adhesive zones 95. Regardless of the adhesive pattern utilized, it is desired that the pattern be selected such that at least a portion of the adhesive pattern will correspond in location to seams 34 (FIG. 1) of training pant 20.

Alternatively, the application of adhesive can be eliminated, and elongated elastic member 88 can be joined to first layer 80 in a subsequent bonding step that results in seams 34, as will be described hereafter. In this case, elongated elastic member 88 will be joined to first layer 80 after folding first layer 80.

After providing elongate elastic member 88 to first layer 80, first layer 80 passes through a folding board 94, which continuously folds first layer 80 in a direction generally transverse to first direction 82 along a fold line 96 and over elongate elastic member 88. Upon being folded, elongate elastic member 88 is intermittently joined to first layer 80, thereby resulting in a first elastic composite 97, which will ultimately form a part of elongate sleeve member 62 (FIG. 2).

A second elastic composite 112 (FIG. 6) can be made in a separate manufacturing assembly line in the same manner as first elastic composite 97. These two elastic composites 97, 112 can be made in a parallel manner to each other, or angularly oriented to each other, depending upon various factors, such as facility accommodations, i.e., the size of the building housing the apparatus, material supply requirements, operator requirements, or the like. After first and second elastic composites 97, 112 have been made, they can be individually wound on rolls, and transported to another assembly line, such as that in FIG. 6, for subsequent handling.

Referring now to FIG. 6, a base layer 98 having opposite edge portions 102, 104 is continuously moved in a machine direction 100. Base layer 98 may be a single layer of material, or a laminate or composite comprising, for example in this description, two layers that ultimately form outer layer 50 and inner layer 52 (FIG. 2). Base layer 98 may also be made of a material suitable for use as liner 48. A pair of adhesive applicators, such as adhesive spray nozzles 106, apply adhesives, such as adhesives 74 (FIG. 2), along opposite edge portions 102, 104.

A plurality of absorbent structures 38 are registered or provided on top of base layer 98 at equidistantly spaced apart locations between the opposite edge portions 102, 104. Absorbent structures 38 are positioned on base layer 98 such that their respective lengths 42 are transverse to machine direction 100. This orientation of absorbent structures 38 also results in their respective widths 44 being transverse to the cross direction 101. Each length 42 is greater in dimension than a width 44. The absorbent structures 38 can be provided in any suitable manner known in the art.

A top layer 108 is continuously supplied on top of absorbent structures 38 and base layer 98. Just as base layer 98 may be made of a material or layers of material suitable for outer cover layer 46 or liner 48, top layer 108 may also be made of materials suitable for use as outer cover layer 46 or liner 48. In this particular description, top layer 108 is the liner. First elastic composite 97 and second elastic composite 112 are continuously delivered to base layer 98 so as to be positioned on respective edge portions 102, 104, and are joined thereto by adhesive beads 74 (FIG. 2). A pressure roller 110 presses elastic composites 97, 112, base layer 98, and, if desired, top layer 108, together to assist in joining the layers together. Top layer 108 may be smaller in transverse width than base layer 98, and thus may not be in contact with elastic composites 97, 112. The elastic composites 97, 112 will form elongate sleeve member 62 (FIG. 2).

Elastic composites 97, 112 may be joined to either side of base layer 98. For example, FIG. 6 illustrates the elastic composites 97, 112 joined on the same side of base layer 98 on which absorbent structures 38 are placed. If desired, elastic composites 97, 112 can be joined on the opposite side of base layer 98, thereby resulting in the embodiment in FIG. 2.

A patterned rotary die, such as patterned cutting roll 114, cuts a plurality of openings 116 through top layer 108 and base layer 98, between absorbent structures 38. Openings 116 will subsequently form leg openings 32 (FIG. 1). If desired, openings 116 can be formed by other means, such as by water-jet cutters, and may be cut into any desired form.

Thereafter, a folding board 118 folds base layer 98 along a fold line 120 that is parallel to the machine direction 100. A rotary ultrasonic bonder 122 then bonds the folded base layer 98 along a plurality of bond lines 124, which are generally transverse to machine direction 100. The bonding along bond lines 124 forms seams 34 (FIG. 1), and may be continuous or intermittent along one or a plurality of lines. The bond lines 124 are located between absorbent structures 38, and if desired can simultaneously bond each elongate elastic member 88 (FIG. 5) to its respective layer 80 (FIG. 5). In this latter case, it may be unnecessary to apply any adhesive to first layer 80 (FIG. 5).

A cutting roll 126 having a blade 128 cuts base layer 98 along cut lines 130 that are transverse to machine direction 100 and between absorbent structures 38. Desirably, cut lines 130 are located within a central region or area of respective bond lines 124, thereby splitting a single bond line 124 into two bond lines. The cutting of base layer 98 results in a plurality of disposable absorbent training pants 20 having waist elastic systems 60 about waist openings 30, and leg openings 32 formed by seams 34.

In the above-described process, elastic composites 97, 112 are material independent of chassis 22. Thus, elastic composites 97, 112 can be made of any desired materials, and materials different from any materials of which chassis 22 is made, to provide a waist elastic system 60 having desired elastic properties.

Figure 3:
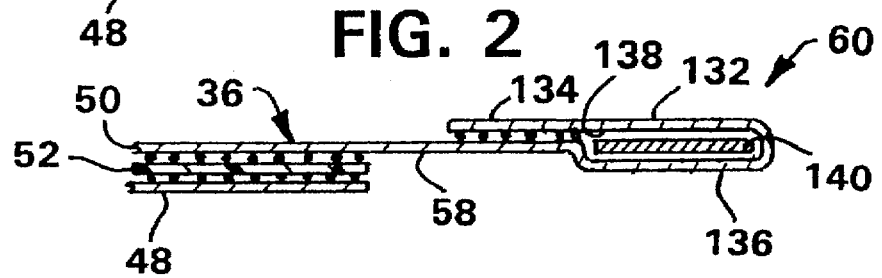
FIG. 3 illustrates a cross-section through the waist of a modification of the pant in FIG. 1.

FIG. 3 illustrates a modification of waist elastic system 60 is integral or unitary with chassis 22 (FIG. 1). In this description, structural elements in common with those in FIG. 2 will retain the same reference numerals. Waist border 36 (FIG. 3) comprises outer layer 50 and inner layer 52. A peripheral edge portion 58 of outer layer 50 extends outwardly, i.e., further to the right as illustrated in FIG. 3, beyond the ends of inner layer 52 and liner 48. Peripheral edge portion 58 extends sufficiently to permit it to be folded upon itself to form an elongate sleeve member 132. Sleeve member 132 comprises an outer surface 134, an inner surface 136, and defines an elongate passage 138 having elongate elastic member 140 disposed therein.

This construction of waist elastic system 60 provides similar advantages and benefits previously described with reference to FIG. 2. With regard to these constructions, the elongate sleeve members 62, 132 can be disposed on the outermost side of outer layer 50 or the innermost side of outer layer 50. For example, in FIG. 2, both outer surface 68 and inner surface 70 of elongate sleeve member 62 can be disposed on the opposite side, the lower side as viewed in FIG. 2, of outer layer 50. Furthermore, if desired, outer surface 68 and inner surface 70 can have peripheral edge portion 58 sandwiched therebetween. With reference to FIG. 3, peripheral edge portion 58 can be folded upon itself in a direction opposite to that illustrated in FIG. 3, such that outer surface 134 is on the opposite side, the lower side as viewed in FIG. 3, of peripheral edge portion 58. Generally, the construction and placement of waist elastic system 60 with reference to peripheral edge portion 58 will be determined by several factors, such as material factors, manufacturing factors, aesthetic factors, or the like.

Figure 4:
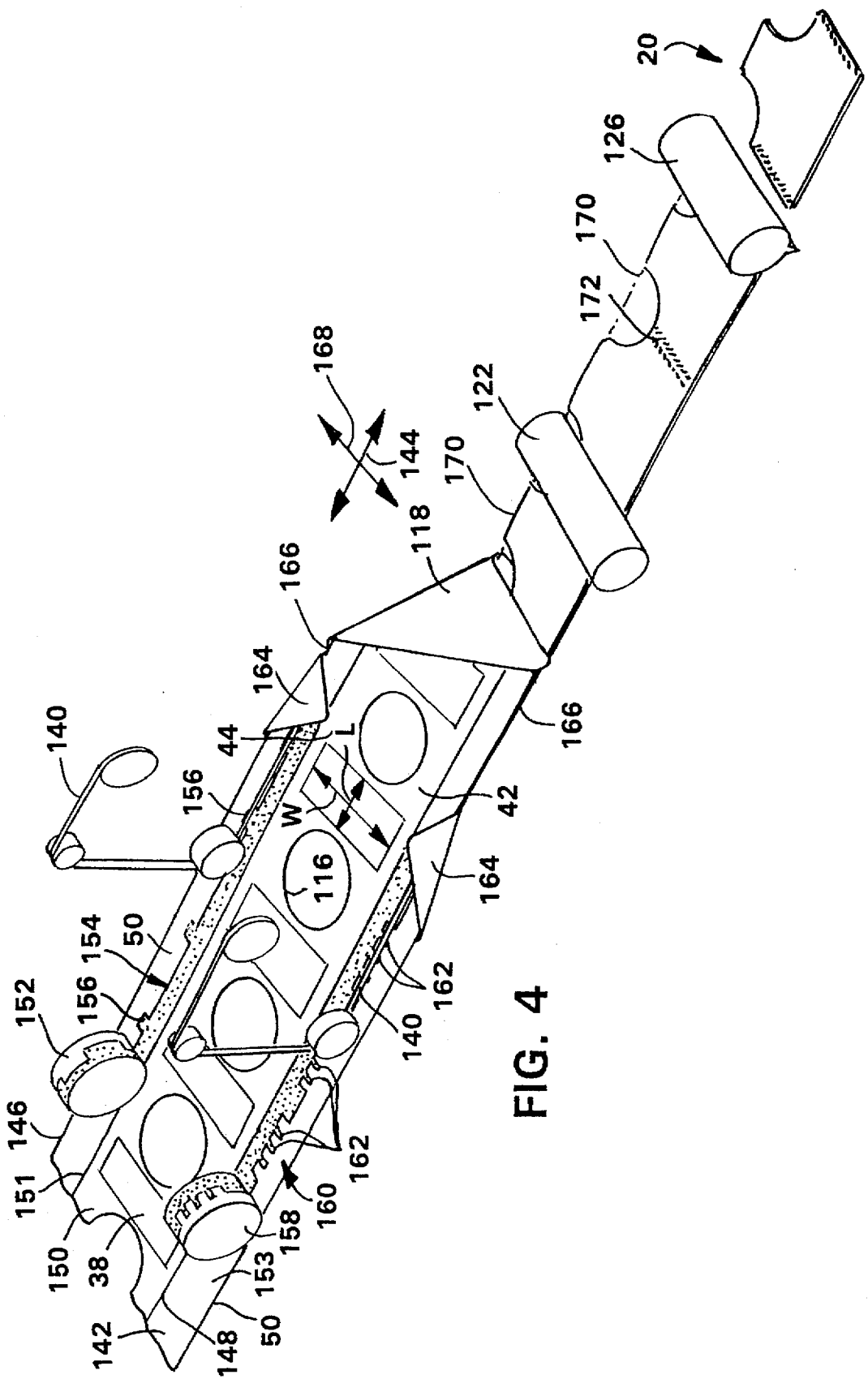
FIG. 4 is a schematic diagram illustrating one process for making a training pant similar to that represented in FIG. 3.

With reference to FIG. 4, a description will be made of one process for making the modification in FIG. 3. A base layer 142 having opposite edge portions 146, 148 is continuously moved in a machine direction 144. Base layer 142 may be any of the layers previously described with reference to chassis 22. For example, base layer 142 may be selected to eventually comprise outer cover layer 46, liner 48, or any other layer that may be incorporated in chassis 22. In this particular description, base layer 142 is selected to be outer cover layer 46 comprising an outer layer 50 and an inner layer 52.

A plurality of absorbent structures 38 are registered or provided on top of base layer 142 in an equidistantly spaced-apart manner. Each absorbent structure 38 has a length dimension 42 greater than a width dimension 44, and is oriented on base layer 142 such that length dimension 42 is generally transverse to machine direction 144. The absorbent structures 38 are also, as illustrated in FIG. 4, positioned between opposite edge portions 146, 148 of base layer 142.

A top layer 150, such as a liner material in this description, is continuously supplied, in any suitable manner well known in the art, to overlay the absorbent structures 38 and base layer 142, and a plurality of openings 116 are cut or formed in a manner such as that earlier described with reference to FIG. 6.

Top layer 150 has opposite edge portions 151, 153 which, like opposite edge portions 146, 148 of base layer 142, extend in the machine direction 144. As described above, base layer 142 forms outer cover layer 46 comprising outer layer 50 and inner layer 52 (FIG. 3), and outer layer 50 extends laterally beyond opposite edge portions 151, 153 of top layer 150. "Laterally beyond" refers to a direction parallel to cross direction 168, which is transverse to machine direction 144. It is this extension of outer layer 50 that will form a part of waist elastic system 60.

In FIG. 4, two differently patterned adhesive rolls 152, 158 are illustrated for purposes of description intermittently applying different adhesive patterns to base layer 142. However, it is understood that generally only one adhesive pattern will be selected.

Patterned adhesive roll 152 intermittently applies adhesive in machine direction 144 in a selected adhesive pattern 154 to opposite edge portion 146 of base layer 142. Adhesive pattern 154 includes a plurality of distinct adhesive zones 156 which are spaced apart from one another, i.e., intermittently applied, in the machine direction 144. If desired, only distinct adhesive zones 156 can be applied by patterned adhesive roll 152, thereby eliminating any connecting adhesive pattern between the adhesive zones 156. As will be described hereafter, it is the distinct adhesive zones 156 that adhesively join an elongate elastic member 140. The remaining adhesive of adhesive pattern 154 will adhesively join a folded portion of opposite edge portion 146. If preferred, a pulsed adhesive system, similar to pulsed adhesive system 90 in FIG. 5, can replace patterned adhesive rolls 152, 158. Regardless of the apparatus and method of applying adhesives, it is important that the process and apparatus be capable of applying the adhesive in a selectively intermittent pattern.

Patterned adhesive roll 158 applies an optional adhesive pattern 160 having a plurality of spaced-apart distinct adhesive zones 162. In comparison to adhesive zones 156, adhesive zones 162 are more closely spaced together. The spacing of adhesive zones 156, 162, as well as their dimensions, can be dependent upon numerous variables, such as the adhesive material, the amount of adhesive applied, the elastic material, the layer materials, manufacturing speeds, or the like.

An elongate elastic member 140 is continuously delivered, in machine direction 144, to each edge portion 146, 148 of base layer 142. In this particular description, these opposite edge portions 146, 148 correspond to, in the finished product, peripheral edge portion 58 (FIG. 3) of outer layer 50. Each elongate elastic member 140 can be applied either with a selected tension, or substantially untensioned, in a manner similar to that described with reference to the method in FIG. 6.

As illustrated in FIG. 4, each of the elongate elastic members 140 are delivered or positioned on base layer 142 such that they overlie adhesive zones 156 in opposite edge portion 146, or adhesive zones 162 in opposite edge portion 148. This results in an intermittent joining of elastic members 140 in their respective edge portions 146, 148.

After elongate elastic members 140 have been delivered to base layer 142, a pair of folding boards 164 fold each opposite edge portion 146, 148 along their respective fold lines 166. This causes each opposite edge portion 146, 148 to be folded in a direction parallel to cross direction 168, and over a respective elongate elastic member 140. Opposite edge portions 146, 148 will eventually form, in a finished training pant 20, an elongate sleeve member 62 (FIG. 2).

After passing through folding boards 164, base layer 142 can be processed in a manner similar to that in FIG. 6. For example, a folding board 118 folds base layer 142 along fold line 170, which is generally parallel to machine direction 144. An ultrasonic bonder, such as rotary ultrasonic bonder 122, ultrasonically bonds folded base layer 142 along a plurality of bond lines 172, generally transverse to machine direction 144. A cutting roll 126 then cuts base layer 142 along a plurality of cut lines that lie between absorbent structures 38 and that are generally transverse to machine direction 144. The cutting of folded base layer 142 forms individual disposable absorbent training pants 20 (FIG. 1) with respective waist elastic systems 60 (FIG. 2) about waist openings 30, and leg openings 32 formed from seams 34.

While this invention has been described as having preferred embodiments, it will be understood that it is capable of further modifications. This application is therefore intended to cover any variations, equivalents, uses or adaptations of the invention following the general principles thereof, and including such departures from the present disclosure as come within known or customary practice in the art to which this invention pertains and falls within the limits of the appended claims.

What is claimed is:

1. A process having a machine direction and a cross direction for making disposable absorbent articles, comprising the steps of:

continuously moving a first layer in a first direction, the first layer having opposite edge portions generally extending in the first direction, continuously providing an elongate elastic member generally in the first direction to the first layer, folding the first layer, in a direction generally transverse to the first direction, over the elongate elastic member, continuously moving a continuously moving a second layer in a second direction, the second layer having opposite edge portions generally extending in the second direction, continuously providing an elongate elastic member generally in the second direction to the second layer, folding the second layer, in a direction generally transverse to the second direction, over the elongate elastic member, continuously moving a base layer in a machine direction, the base layer having opposite edge portions generally extending in the machine direction, continuously delivering the folded first layer to one of the edge portions of the base layer, joining the folded first layer to the one edge portion of the base layer, continuously delivering the folded second layer to the other edge portion of the base layer, joining the folded second layer to the other edge portion of the base layer, providing a plurality of absorbent structures having respective length dimensions greater than respective width dimensions, positioning the absorbent structures at spaced apart locations between the opposite edge portions of the base layer, folding the continuously moving base layer along a fold line generally parallel to the machine direction, bonding the folded, continuously moving base layer along a plurality of bond lines generally transverse to the machine direction, and cutting the bonded, continuously moving base layer along a plurality of cut lines generally transverse to the machine direction and between the spaced apart absorbent structures to form a plurality of disposable articles.

2. The process of claim 1 further comprising the step of forming a waistband in each disposable absorbent article from the folded first and second layers.

3. The process of claim 2 wherein the step of forming a waistband in each disposable absorbent article includes providing each waistband with an average maximum rate of change of modulus of elasticity over the first three cycles of about 1.96 grams per millimeter in an extension range between about 175 millimeters to about 325 millimeters.

4. The process of claim 1 wherein the step of bonding the folded, continuously moving base layer includes bonding the elongate elastic members to their respective folded first and second layers.

5. The process of claim 4 wherein the step of bonding includes ultrasonically bonding the folded, continuously moving base layer.

6. The process of claim 1 wherein the step of providing a plurality of absorbent structures includes positioning the absorbent structures with their respective length dimensions generally transverse to the machine direction.

7. The process of claim 1 wherein the first direction and the second direction are generally parallel to the machine direction.

8. The process of claim 1 wherein the first direction and the second direction are angularly oriented to the machine direction.

* * * * *

UNITED STATES PATENT AND TRADEMARK OFFICE
CERTIFICATE OF CORRECTION

PATENT NO. : 5,711,832
DATED : January 27, 1998
INVENTOR(S) : Frank Steven Glaug and Margaret Ann Kato It is certified that error appears in the above-identified patent and that said Letters Patent is hereby corrected as shown below:

Columns 9 and 10,
Table 1, continued, Average, Extension 3 at 225 mm, delete "180.87" and substitute
-- 180.67 --.
Table 1, continued, Specimen 1, Retraction 3 at 300 mm, delete "249.00" and substitute
-- 249.20 --.
Table 2, Specimen 3, Extension 3 at 175 mm, delete "75.85" and substitute -- 75.65 --.
Table 2, Specimen 4, Extension 3 at 250 mm, delete "233.82" and substitute
-- 233.62 --.

Columns 11 and 12,
Table 3, Specimen 4, Extension 2 at 325 mm, delete "2296.18" and substitute
-- 2296.16 --.
Table 4, Average, Extension 2 at 200 mm, delete "14.88" and substitute -- 14.68 --.

Columns 13 and 14,
Table 4-continued, Specimen 1, Extension 3 at 175 mm, delete "11.12" and substitute
-- 11.12 --.
Table 5, Specimen 1, Extension 1 at 175 mm, delete "422.55" and substitute
-- 422.65 --.
Table 5, Specimen 1, Extension 3 at 275 mm, delete "840.95" and substitute
-- 840.85 --.

Columns 15 and 16,
Table 6, Specimen 5, Extension 1 at 175 mm, delete "-2-22" and substitute -- 2.22 --.
Table 6, Slope, Extension 2 at 300 mm, delete "6.85" and substitute -- 6.65 --.

Columns 19 and 20,
Table 9, Specimen 1, Retraction 2 at 200 mm, delete "133.53" and substitute
-- 133.63 --.

Columns 21 and 22,
Table 10, Embodiment 2, Avg., Extension 1 at 225, delete "224.26" and substitute
-- 224.28 --.
Table 10, Sample 7, Slope, Extension 1 at 225, delete "2.67" and substitute -- 2.87 --.
Table 10, Sample 1, Avg., Extension 1 at 325, delete "1845.15" and substitute
-- 1845.16 --.
Table 10, Sample 7, Avg., Retraction 1 at 300, delete "429.54" and substitute
-- 429.84 --.

UNITED STATES PATENT AND TRADEMARK OFFICE
CERTIFICATE OF CORRECTION

PATENT NO.    : 5,711,832
DATED         : January 27, 1998
INVENTOR(S)   : Frank Steven Glaug and Margaret Ann Kato It is certified that error appears in the above-identified patent and that said Letters Patent is hereby corrected as shown below:

<u>Columns 21 and 22 cont'd,</u>
Table 10, Sample 7, Avg., Retraction 1 at 200, delete "130.05" and substitute
-- 130.06 --.
Table 10, Sample 6, Slope, Extension 2 at 325, delete "1039.53".
Table 10, Sample 7, Avg., Extension 2 at 325, insert -- 1039.63 --.
Table 10, Sample 7, Avg., Retraction 2 at 325, delete "1039.53"and substitute
-- 1039.63 --.
Table 10, Sample 3, Slope, Retraction 2 at 275, delete "7.45" and substitute -- 7.46 --.
Table 10, Sample 6, Avg., Retraction 2 at 225, delete "316.10" and substitute
-- 318.10 --.

<u>Columns 23 and 24,</u>
Table 10-continued, Sample 3, Slope, Extension 3 at 225, delete "6.54" and substitute
-- 6.64 --.

Signed and Sealed this

First Day of October, 2002

*Attest:*

*Attesting Officer*

JAMES E. ROGAN
*Director of the United States Patent and Trademark Office*